United States Patent
Ellis et al.

(10) Patent No.: US 10,927,140 B2
(45) Date of Patent: Feb. 23, 2021

(54) COMPOSITIONS AND METHODS FOR REVERSE AUTOMATED NUCLEIC ACID SYNTHESIS

(71) Applicant: The University of Toledo, Toledo, OH (US)

(72) Inventors: Matthew Ellis, Toledo, OH (US); Amanda Bryant-Friedrich, Toledo, OH (US)

(73) Assignee: The University of Toledo, Toledo, OH (US)

( * ) Notice: Subject to any disclaimer, the term of this patent is extended or adjusted under 35 U.S.C. 154(b) by 0 days.

(21) Appl. No.: 16/384,080

(22) Filed: Apr. 15, 2019

(65) Prior Publication Data

US 2019/0315794 A1 Oct. 17, 2019

Related U.S. Application Data

(60) Provisional application No. 62/658,134, filed on Apr. 16, 2018.

(51) Int. Cl.
*C07H 21/00* (2006.01)
*C07H 19/10* (2006.01)
*C07H 1/00* (2006.01)
*C07H 19/20* (2006.01)

(52) U.S. Cl.
CPC ............... *C07H 19/10* (2013.01); *C07H 1/00* (2013.01); *C07H 19/20* (2013.01); *C07H 21/00* (2013.01)

(58) Field of Classification Search
None
See application file for complete search history.

(56) References Cited

U.S. PATENT DOCUMENTS

| | | | |
|---|---|---|---|
| 6,207,819 B1 * | 3/2001 | Manoharan | C07H 21/00 435/91.1 |
| 2011/0137010 A1 | 6/2011 | Srivastava et al. | |

FOREIGN PATENT DOCUMENTS

| WO | WO-2005028494 A1 * | 3/2005 | ............. C07H 21/04 |
|---|---|---|---|
| WO | 2010027512 A2 | 3/2010 | |
| WO | 2015039053 A2 | 3/2015 | |

OTHER PUBLICATIONS

Somoza Chem. Soc. Rev. (2008), vol. 37, pp. 2668-2675.*
Dey et al. Nature Chemical Biology (2017), vol. 13, pp. 210-217.*
Al-Oudat et al. Bioorganic & Medicinal Chemistry Letters (2013), vol. 23, pp. 854-859.*

* cited by examiner

*Primary Examiner* — Patrick T Lewis
(74) *Attorney, Agent, or Firm* — MacMillan, Sobanski & Todd, LLC

(57) ABSTRACT

Methods for reverse automated nucleic acid synthesis, and 5'-H-phosphonates suitable for use in the same, as well as methods for making 5'-H-phosphonates, are described.

16 Claims, 24 Drawing Sheets

COMPOSITIONS AND METHODS FOR REVERSE AUTOMATED NUCLEIC ACID SYNTHESIS

RELATED APPLICATIONS

This application claims priority to U.S. Provisional Application No. 62/658,134 filed under 35 U.S.C. § 111(b) on Apr. 16, 2018, the disclosure of which is incorporated herein by reference in its entirety.

STATEMENT REGARDING FEDERALLY SPONSORED RESEARCH

This invention was made with government support under Grant Number CHE1309135 awarded by the National Science Foundation. The government has certain rights in this invention.

BACKGROUND

Most methods of oligonucleotide synthesis are in the direction of 3' to 5'. Conventional methods of RNA synthesis in the reverse direction, from 5' to 3', use phosphoramidites and still utilize a 2' O-silyl protecting group with a dimethoxytrityl protecting group at the 3' position. It would be advantageous to discover new and improved compositions useful for, and methods of, synthesizing RNA and other oligonucleotides in the reverse direction, from 5' to 3'.

SUMMARY

Provided is a composition having Formula I:

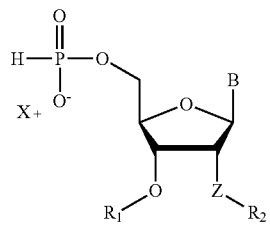

Formula I wherein X is a trialkylammonium having a formula of $NHR_3$, wherein $R_3$ is alkyl; Z is oxygen, nitrogen, or fluorine; $R_1$ is a protecting group; $R_2$ is tert butyl dimethyl silyl (TBDMS), triisopropylsilyl oxymethylene, fluorenylmethyloxycarbonyl (Fmoc), alkyl, aryl, or acetyl; and B is hydrogen, a nucleobase, aryl, or a heterocycle optionally protected. Also provided are stereoisomers, racemates, hydrates, solvates, polymorphs, and prodrugs of Formula I.

In certain embodiments, there is no protecting group on the phosphonate of Formula I.

In certain embodiments, $R_1$ comprises dimethoxytrityl, monomethoxytrityl, or trimethoxytrityl.

In certain embodiments, the composition comprises Formula II:

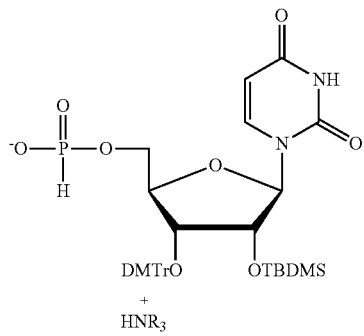

Formula II

In certain embodiments, the composition comprises Formula III:

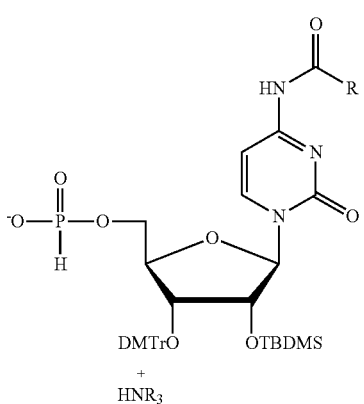

Formula III wherein R is phenyl or isobutyl.

In certain embodiments, the composition comprises Formula IV:

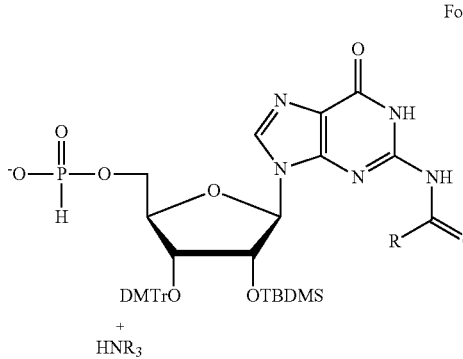

Formula IV wherein R is phenyl or isobutyl.

In certain embodiments, the composition comprises Formula V:
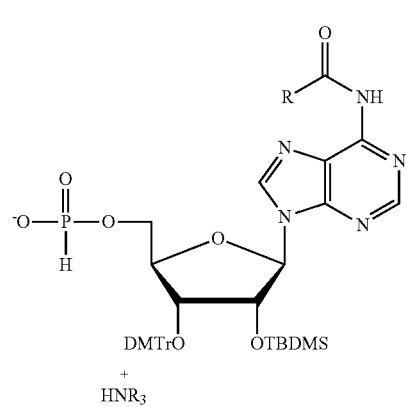
Formula V
wherein R is phenyl or isobutyl.
In certain embodiments, the composition comprises compound 95:
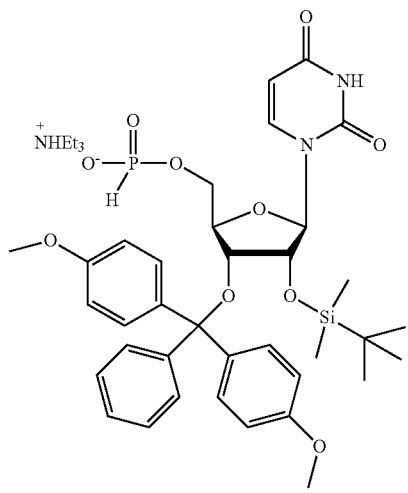
95
In certain embodiments, the composition comprises compound 127:
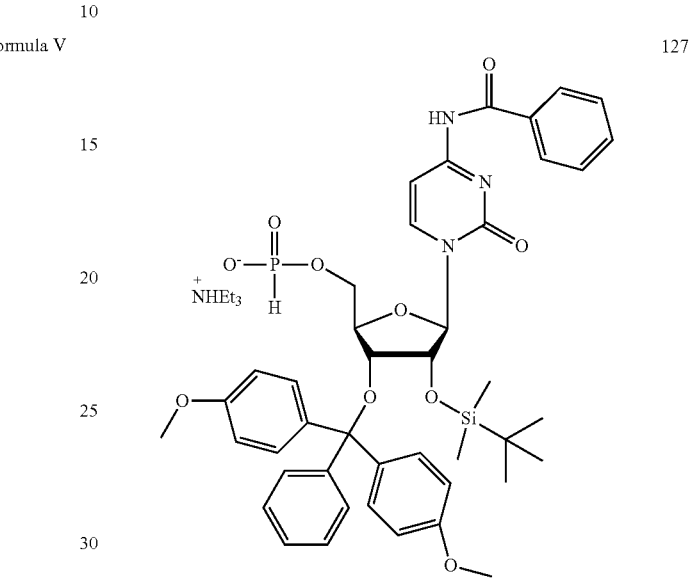
127
In certain embodiments, the composition comprises compound 135:
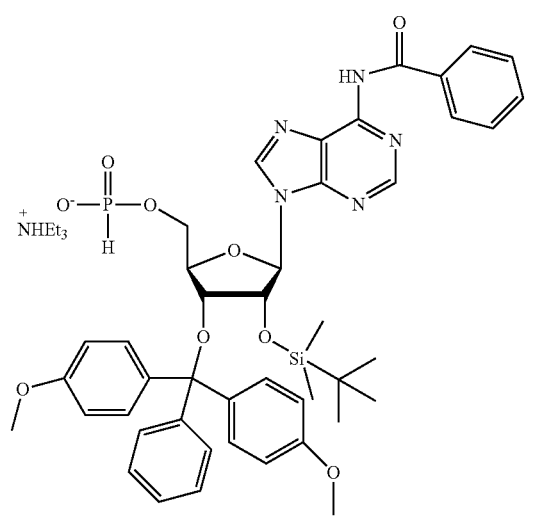
135

In certain embodiments, the composition comprises compound 143:

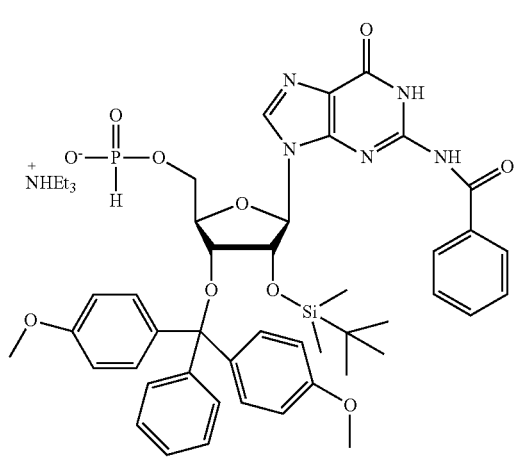

Further provided is a method for synthesizing an oligonucleotide, the method comprising linking a protected first nucleoside through a first linker to a support to form a support-bound nucleoside, treating the support with a halogenated carboxylic acid in dichloromethane to free a 3' hydroxyl of the support-bound nucleoside, coupling a second nucleoside to the first nucleoside to form a first H-phosphonate linkage, wherein the second nucleoside comprises a 5'-H-phosphonate prior to the coupling, capping unreacted 3' ends by esterification to incorporate capping groups thereon, oxidizing the first H-phosphonate linkage to produce an oligonucleotide, and, optionally, repeating the deprotection, coupling, capping, and oxidizing steps to produce an oligonucleotide having a desired sequence.

In certain embodiments, the second nucleoside is activated prior to coupling with adamantyl chloride. In certain embodiments, the second nucleoside is a 3'-dimethoxytrityl-5'-H-phosphonate salt prior to the coupling.

In certain embodiments, the repeating comprises coupling a third nucleoside to the second nucleoside to form a second H-phosphonate linkage, wherein the third nucleoside comprises a 5'-H-phosphonate prior to the coupling.

In certain embodiments, the method further comprises removing the support.

In certain embodiments, the method further comprises subjecting the oligonucleotide to a silyl deprotection step.

In certain embodiments, the protected first nucleoside comprises a 3'-DMTr protected nucleoside.

In certain embodiments, the second nucleoside is activated using a bulky carboxylic acid chloride.

In certain embodiments, the method further comprises oxidizing the first H-phosphonate linkage. In particular embodiments, the first H-phosphonate linkage is oxidized with $I_2$, $H_2O$, pyridine, or THF. In particular embodiments, the oxidizing is conducted prior to addition of a third nucleoside. In particular embodiments, the oxidizing is conducted following addition of a third or subsequent nucleoside.

In certain embodiments, the esterification is either (i) with excess acid chloride left after the coupling or (ii) with acetic anhydride/pyridine.

In certain embodiments, the method further comprises removing the capping groups.

In certain embodiments, the 5'-H-phosphonate comprises Formula I:

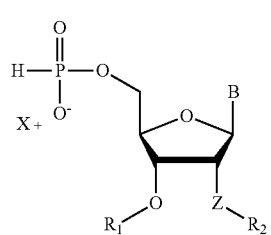

wherein X is a trialkylammonium having a formula of $NHR_3$, wherein $R_3$ is alkyl; Z is oxygen, nitrogen, or fluorine; $R_1$ is a protecting group; $R_2$ is tert butyl dimethyl silyl (TBDMS), triisopropylsilyl oxymethylene, fluorenylmethyloxycarbonyl (Fmoc), alkyl, aryl, or acetyl; and B is hydrogen, a nucleobase, aryl, or a heterocycle optionally protected; or a stereoisomer, racemate, hydrate, solvate, polymorph, or prodrug thereof.

In certain embodiments, the 5'-H-phosphonate comprises Formula II:

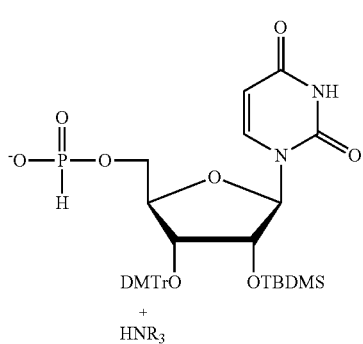

In certain embodiments, the 5'-H-phosphonate comprises Formula III:

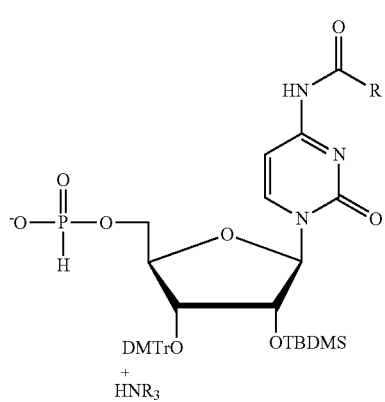

wherein R is phenyl or isobutyl.

In certain embodiments, the 5'-H-phosphonate comprises Formula IV:

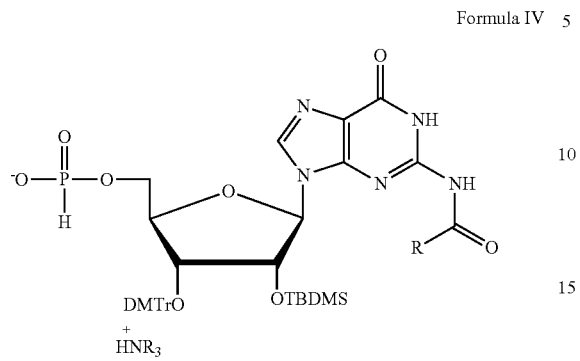

Formula IV wherein R is phenyl or isobutyl.

In certain embodiments, the 5'-H-phosphonate comprises Formula V:

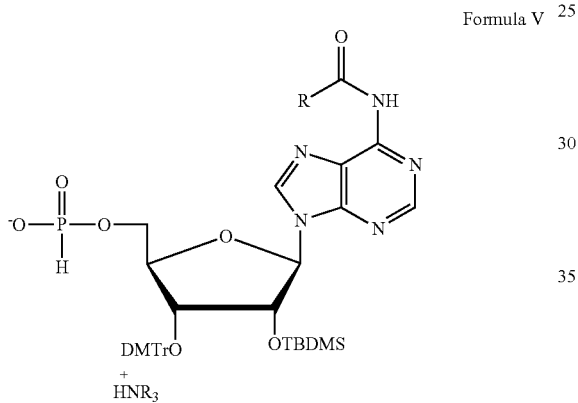

Formula V wherein R is phenyl or isobutyl.

In certain embodiments, the 5'-H-phosphonate comprises compound 95:

In certain embodiments, the 5'-H-phosphonate comprises compound 127:

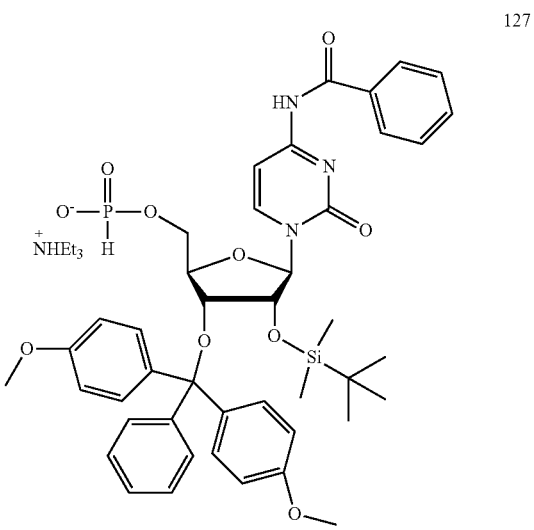

127

In certain embodiments, the 5'-H-phosphonate comprises compound 135:

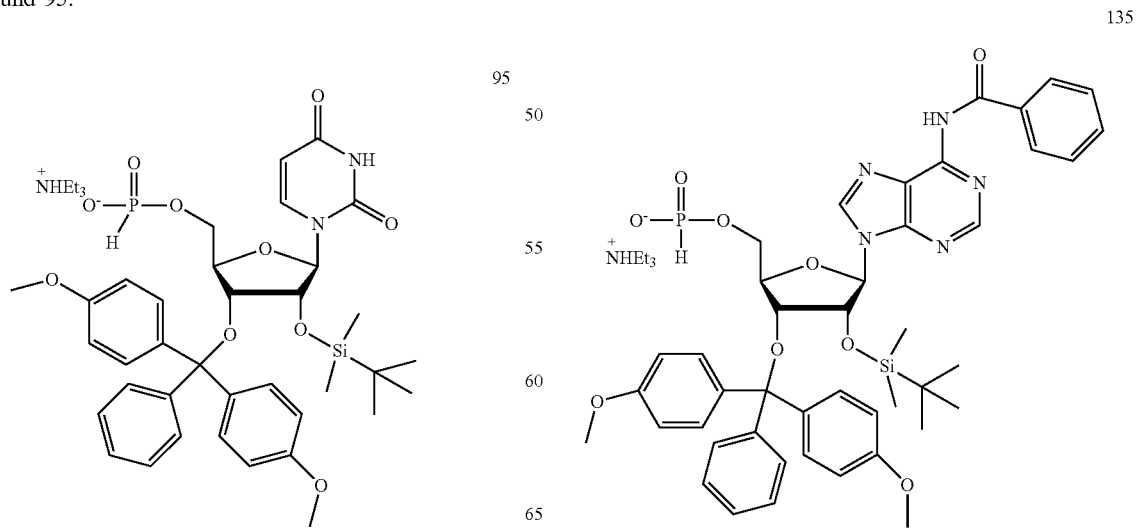

95

135

In certain embodiments, the 5'-H-phosphonate comprises compound 143:

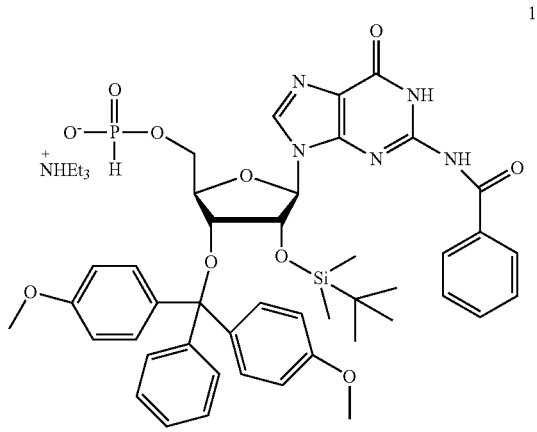

Further provided is a method for making a 5'-H-phosphonate, the method comprising protecting a nucleoside at a 2' position with a first protecting group to form a 2'-protected nucleoside; protecting the 2'-protected nucleoside at a 5' position to form a fully protected nucleoside; hydrolyzing the fully protected nucleoside in acid with heat to form a hydrolyzed protected nucleoside; silylating the hydrolyzed protected nucleoside at the 2' position to form a silylated nucleoside; protecting the silylated nucleoside with a second protecting group to form a protected silylated nucleoside; deprotecting the protected silylated nucleoside to form a 5' hydroxyl nucleoside; and phosphonating the 5' hydroxyl nucleoside to form a 5'-H-phosphonate. In certain embodiments, the 5'-H-phosphonate comprises Formula I.

In certain embodiments, the nucleoside comprises uridine. In particular embodiments, the first protecting group comprises tetrabutylammonium tribromide (TBATB). In particular embodiments, the protecting the 2'-protected nucleoside comprises reacting the protected nucleoside with benzoyl chloride in pyridine. In particular embodiments, acid is 25% acetic acid. In particular embodiments, the silylating is a selective silylation at the 2' position using tert-butyldimethylsilyl chloride and silver nitrate in a mixture of pyridine and tetrahydrofuran. In particular embodiments, the second protecting group comprises dimethoxytrityl chloride. In particular embodiments, the deprotecting comprises reacting the protected silylated nucleoside with 2N sodium hydroxide in pyridine and methanol. In particular embodiments, the phosphonating comprises reacting the 5'hydroxyl nucleoside with phosphorous trichloride, imidazole, and trimethylamine in dichloromethane.

In certain embodiments, the nucleoside comprises cytidine. In particular embodiments, protecting the nucleoside at the 2' position comprises reacting the nucleoside with perchloric acid in acetone. In particular embodiments, the protecting the nucleoside at the 5' position comprises reacting the 2'-protected nucleoside with benzoyl chloride in pyridine. In particular embodiments, the hydrolyzing comprises using dilute HCl in dioxane. In particular embodiments, the method further comprises purifying the fully protected nucleoside prior to the hydrolyzing. In particular embodiments, the silylating comprises reacting the hydrolyzed protected nucleoside with tert-butyldimethylsilyl chloride and silver nitrate in a mixture of pyridine and tetrahydrofuran.

In certain embodiments, the nucleoside comprises adenosine. In particular embodiments, protecting the nucleoside at the 2' position comprises reacting the nucleoside with perchloric acid in acetone. In particular embodiments, the protecting the 2'-protected nucleoside comprises benzoylating the protected nucleoside at the 5' position as well as on an exocylic amine using benzoyl chloride in pyridine. In particular embodiments, the hydrolyzing comprises using dilute HCl in dioxane. In particular embodiments, the silylating comprise using tert-butyldimethylsilyl chloride and silver nitrate in a mixture of pyridine and tetrahydrofuran. In particular embodiments, the second protecting group comprises dimethoxytrityl chloride.

In certain embodiments, the nucleoside comprises guanosine. In particular embodiments, protecting the nucleoside at the 2' position comprises reacting the nucleoside with perchloric acid in acetone. In particular embodiments, the protecting the 2'-protected nucleoside at the 5'-position comprises benzoylating the 2'-protected nucleoside at the 5' position as well as on an exocyclic amine using benzoyl chloride in pyridine. In particular embodiments, the hydrolyzing comprises using dilute HCl in dioxane. In particular embodiments, the silylating comprises silylating the hydrolyzed protected nucleoside at the 2' position using tert-butyldimethylsilylchloride and silver nitrate in a mixture of pyridine and tetrahydrofuran. In particular embodiments, the method further comprises purifying the fully protected nucleoside, or washing the fully protected nucleoside with a saturated sodium bicarbonate solution and brine, prior to the hydrolyzing. In particular embodiments, the second protecting group comprises dimethoxytrityl chloride. In particular embodiments, protecting the 2'-protected nucleoside comprises protecting the 2'-protected nucleoside with isobutyryl by reacting the 2'-protected nucleoside with isobutyric anhydride in pyridine. In particular embodiments, the method comprises transiently protecting hydroxyl groups on the guanosine using trimethylsilyl chloride in pyridine. In particular embodiments, the deprotecting comprises adding water or methanol, and THF with trifluoroacetic acid.

Further provided is a kit for conducting oligonucleotide synthesis, the kit comprising a first container housing a 5'-H-phosphonate, and a second container housing a support-bound nucleoside. In certain embodiments, the kit further comprises one or more of a halogenated carboxylic acid, an esterification agent, an oxidizing agent, or a protecting group.

BRIEF DESCRIPTION OF THE DRAWINGS

The patent or application file may contain one or more drawings executed in color and/or one or more photographs. Copies of this patent or patent application publication with color drawing(s) and/or photograph(s) will be provided by the U.S. Patent and Trademark Office upon request and payment of the necessary fees.

DETAILED DESCRIPTION

Figure 1:
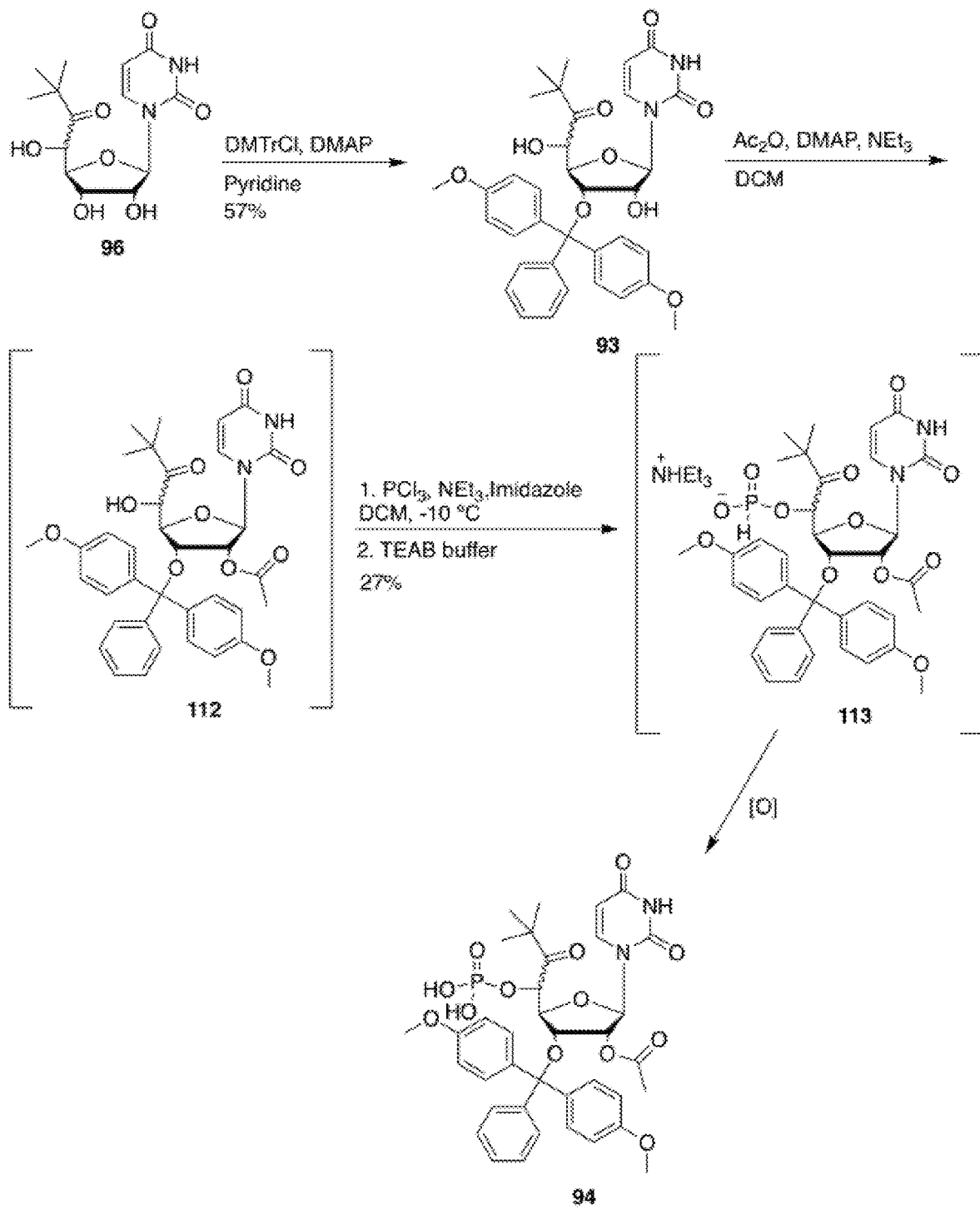
FIG. 1: Scheme 1, showing the synthesis of uridine 5'-H-phosphonate radical precursor.

Throughout this disclosure, various publications, patents, and published patent specifications are referenced by an identifying citation. The disclosures of these publications, patents, and published patent specifications are hereby incorporated by reference into the present disclosure in their entirety to more fully describe the state of the art to which this invention pertains.

DEFINITIONS

For convenience, certain terms are defined, and certain concepts are established, prior to further description of the present disclosure.

Unless stereochemistry is specifically indicated, all stereoisomers of the compounds herein are included, as pure compounds as well as mixtures thereof. It will be appreciated by one of ordinary skill in the art that asymmetric centers may exist in any of the compounds disclosed herein. Thus, the compounds and compositions thereof may be in the form of an individual enantiomer, diastereomer, or geometric isomer, or may be in the form of a mixture of stereoisomers. In certain embodiments, the compounds herein are enantiopure compounds. In certain other embodiments, mixtures of stereoisomers or diastereomers are provided. Additionally, the compounds encompass both (Z) and (E) double bond isomers (or cis and trans isomers) unless otherwise specifically designated. Thus, compounds generally depicted in structures herein encompass those structures in which double bonds are (Z) or (E).

The term "composition" as used herein is intended to encompass a product comprising the specified ingredients in the specified amounts, as well as any product that results, directly or indirectly, from combinations of the specified ingredients in the specified amounts.

The term "solvate" refers to a pharmaceutically acceptable solid form of a specified compound containing solvent molecules as part of the crystal structure. A solvate typically retains at least some of the biological effectiveness of such compound. Solvates can have different solubilities, hygroscopicities, stabilities, and other properties. Examples of solvates include, but are not limited to, compounds in combination with water, isopropanol, ethanol, methanol, DMSO, ethyl acetate, acetic acid, or ethanolamine Solvates are sometimes termed "pseudopolymorphs."

The term "hydrate" refers to a solvate with water.

The term "racemate" refers to a mixture that contains an equal amount of enantiomers.

The term "polymorph" means a crystalline form of a substance that is distinct from another crystalline form of the substance but that shares the same chemical formula.

It will be appreciated that any of the compounds described herein may be substituted with any number of substituents or functional moieties. In general, the term "substituted," whether preceded by the term "optionally" or not, and substituents contained in formulas, refer to the replacement of hydrogen atoms in a given structure with a specified substituent. When more than one position in any given structure may be substituted with more than one substituent selected from a specified group, the substituent may be either the same or different at every position. The term "substituted" is contemplated to include all permissible substituents of organic compounds. In a broad aspect, the permissible substituents include acyclic and cyclic, branched and unbranched, carbocyclic and heterocyclic, aromatic and nonaromatic substituents or organic compounds. For purposes of explanation herein, heteroatoms such as nitrogen may have hydrogen substituents and/or any permissible substituents of organic compounds described herein which satisfy the valencies of the heteroatoms. Furthermore, there is not any intention to be limited in any manner by the permissible substituents of organic compounds.

The term "alkyl" refers to monovalent alkyl groups having from 1 to 50 carbon atoms, preferably having from 1 to 10 carbon atoms, and more preferably having from 1 to 6 carbon atoms. This term is exemplified by groups such as methyl, ethyl, n-propyl, iso-propyl, n-butyl, iso-butyl, n-hexyl, and the like. "Substituted alkyl" refers to an alkyl group, preferably of from 1 to 10 carbon atoms, having from 1 to 3 substituents selected from the group consisting of alkoxy, substituted alkoxy, acyl, acylamino, amino, aminoacyl, aminocarboxy esters, cyano, cycloalkyl, halogen, hydroxyl, carboxyl, carboxylalkyl, oxyacyl, oxyacylamino, thiol, thioalkoxy, substituted thioalkoxy, aryl, heteroaryl, heterocyclic, aryloxy, thioaryloxy, heteroaryloxy, thioheteroaryloxy, nitro, mono- and di-alkylamino, mono- and di-(substituted alkyl)amino, mono- and di-arylamino, mono- and di-heteroarylamino, mono- and di-heterocyclic amino, and unsymmetric di-substituted amines having different substituents selected from alkyl, substituted alkyl, aryl, heteroaryl, and heterocyclic.

The term "aryl" refers to an unsaturated aromatic carbocyclic group, preferably of from 6 to 14 carbon atoms, having a single ring (e.g., phenyl) or multiple condensed rings (e.g., naphthyl or anthryl), preferably having from 1 to 3 rings. Some example aryls include phenyl, naphthyl, and the like. Unless otherwise constrained by the definition for the aryl substituent, such aryl groups can optionally be substituted with from 1 to 3 substituents selected from the group consisting of hydroxy, acyl, alkyl, alkoxy, alkenyl, alkynyl, substituted alkyl, substituted alkoxy, substituted alkenyl, substituted alkynyl, amino, aminoacyl, aminocarboxy esters, alkaryl, aryl, aryloxy, carboxyl, carboxylalkyl, acylamino, cyano, halo, nitro, heteroaryl, heterocyclic, oxyacyl, oxyacylamino, thioalkoxy, substituted thioalkoxy, trihalomethyl, mono- and di-alkylamino, mono- and di-(substituted alkyl)amino, mono- and di-arylamino, mono- and di-heteroarylamino, mono- and di-heterocyclic amino, and unsymmetric di-substituted amines having different substituents selected from alkyl, substituted alkyl, aryl, heteroaryl, heterocyclic, and the like. Some example substituents include alkyl, alkoxy, halo, cyano, nitro, trihalomethyl, and thioalkoxy.

The term "acetyl" refers to an acyl group having the formula CH₃CO.

The terms "heteroaryl" or "hetaryl" refer to a group that is both heterocyclic and aromatic.

The term "aralkyl" refers to a group derived from an alkyl radical by replacing one or more hydrogen atoms with aryl groups. Thus, the term "aralkyl" refers to alkylene-aryl groups. In some examples, aralkyl groups have from 1 to 10 carbon atoms in the alkylene moiety and from 6 to 10 carbon atoms in the aryl moiety, however other aralkyl groups are entirely possible and encompassed within the present disclosure.

The term "trityl" refers to a triphenylmethyl radical or group. For example, trityl chloride is also known as triphenylmethyl chloride ($C_{19}H_{15}Cl$). Other example trityl groups include dimethoxytrityl, monomethoxytrityl, or trimethoxytrityl.

The term "silyl" refers to a radical or group having a silicon linkage between it and the carbon atom to which it is attached.

The terms "DMT" and "DMTr" each refer to 4,4'-dimethyoxytrityl.

The term "TBDMS" refers to tert butyl dimethyl silyl.

The term "TBATB" refers to tetrabutylammonium tribromide.

The term "Fmoc" refers to fluorenylmethyloxycarbonyl.

General Description

Provided are compositions and methods for reverse automated oligonucleotide synthesis. In general, the reverse automated oligonucleotide synthesis utilizes compositions having Formula I:

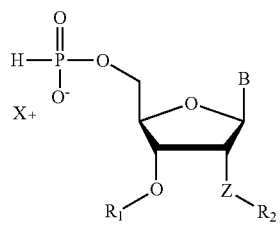

Formula I wherein X is a trialkylammonium having a formula of $NHR_3$, wherein $R_3$ is alkyl; Z is oxygen, nitrogen, or fluorine; $R_1$ is a protecting group; $R_2$ is tert butyl dimethyl silyl (TBDMS), triisopropylsilyl oxymethylene, fluorenylmethyloxycarbonyl (Fmoc), alkyl, aryl, or acetyl; and B is hydrogen, a nucleobase, aryl, or a heterocycle optionally protected. Suitable protecting groups for $R_1$ or $R_2$ include, but are not limited to, dimethoxytrityl (DMTr) protecting groups, such as 4,4'-dimethoxytrityl; monomethoxytrityl; trimethoxytrityl; isobutyryl; acetyl; phenoxyacetyl; allyloxycarbonyl (AOC); aryloxybenzoinyl groups; thiocarbon protecting groups; or silyl ether protecting groups such as trimethylsilyl ether (TMS), trimethylsilyl ether (TES), tert-butyldimethylsilyl ether (TBS/TBDMS), tert-butyldiphenylsilyl ether (TBDPS), or triisopropylsilyl ether (TIPS). The compositions of Formula A are referred to as H-phosphonates.

In some embodiments, the compositions of Formula I are compositions of Formula II:

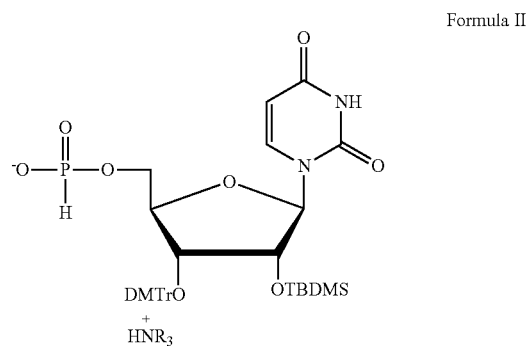

Formula II where R is phenyl or isobutyl. One non-limiting example composition of Formula II is compound 95:

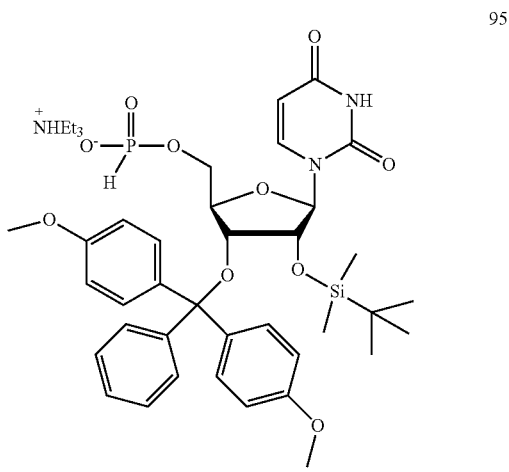

95

Compound 95 is also referred to as ((2R,3R,4R,5R)-3-(bis(4-methoxyphenyl)(phenyl)methoxy)-4-((tertbutyldimethylsilyl)oxy)-5-(2,4-dioxo-3,4-dihydropyrimidin-1(2H)-yl)tetrahydrofuran-2-yl)methyl phosphonate triethylammonium salt. Compound 95 can be synthesized, for example, according to the scheme shown in FIG. 2 and described in detail in the examples herein.

In some embodiments, the compositions of Formula I are compositions of Formula III:

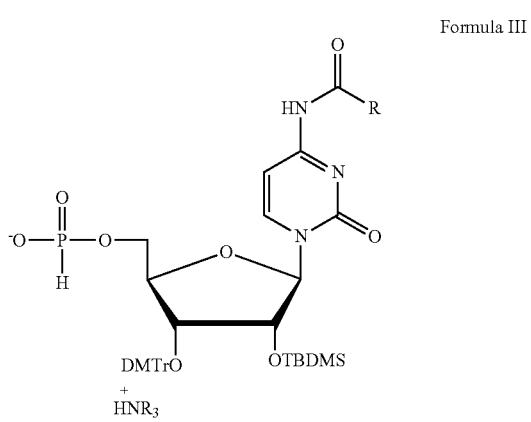

Formula III where R is phenyl or isobutyl. One non-limiting example composition of Formula III is compound 127:

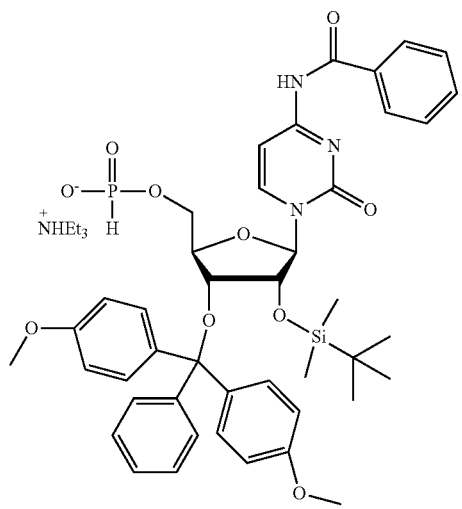

127

Figure 3:
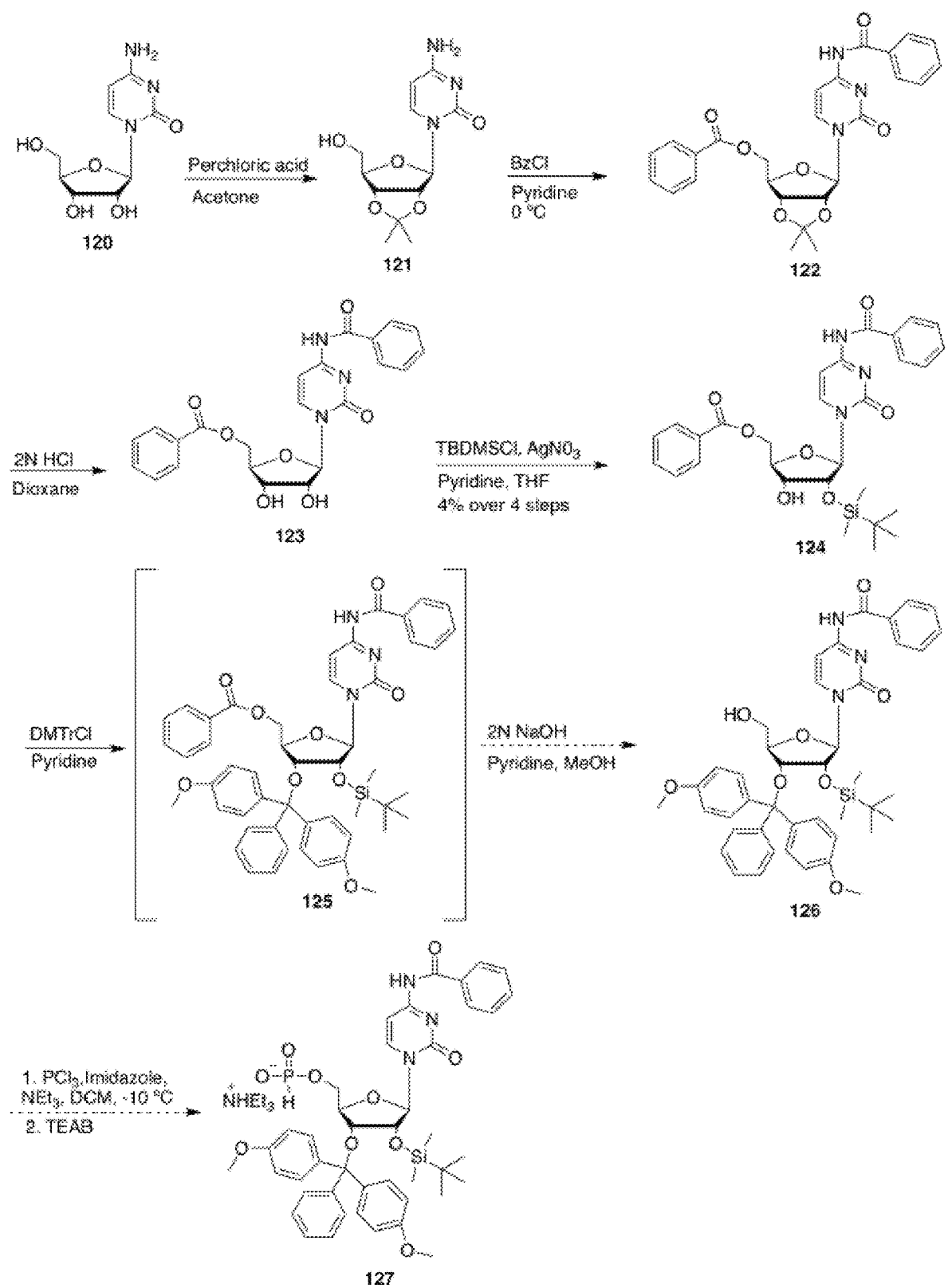
FIG. 3: Scheme 3, showing the synthesis of cytidine 5'-H-phosphonate.

Compound 127 can be prepared, for example, according to the scheme depicted in FIG. 3.

In some embodiments, the compositions of Formula I are compositions of Formula IV:

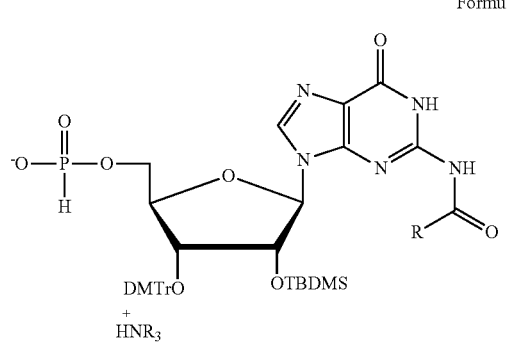

Formula IV where R is phenyl or isobutyl. One non-limiting example composition of Formula IV is compound 135:

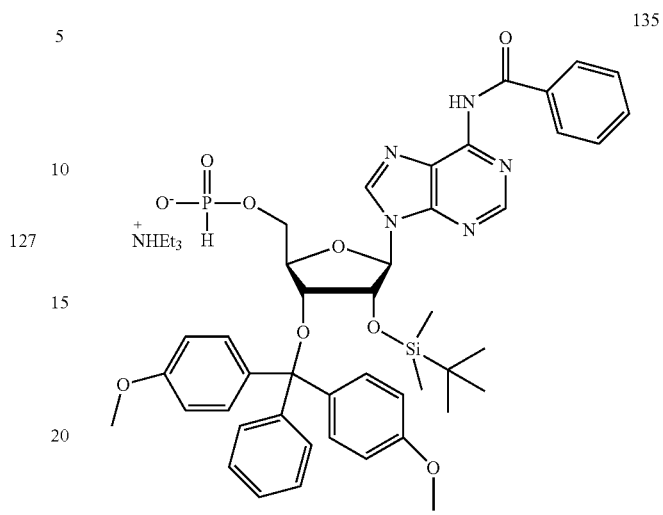

135

Figure 4:
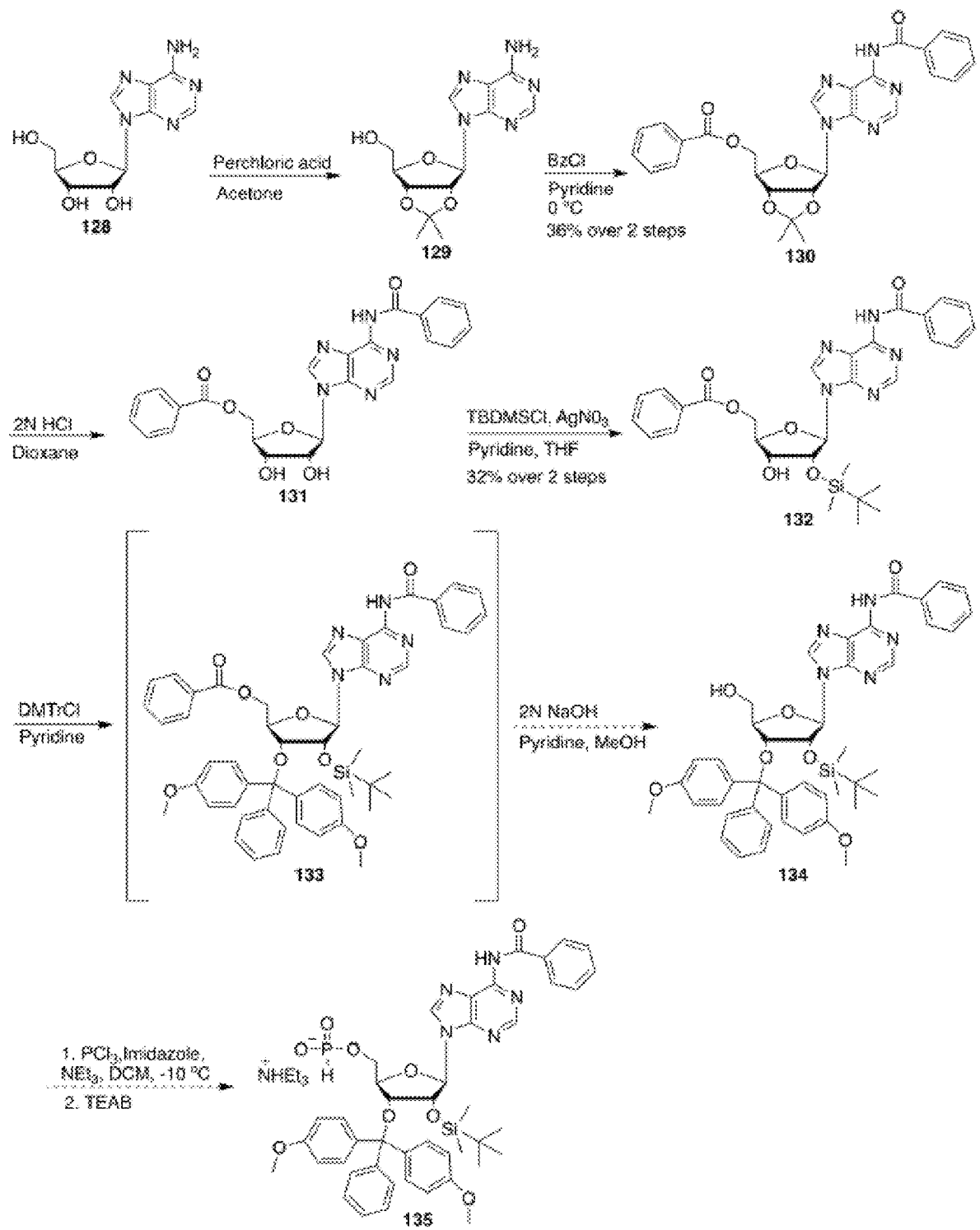
FIG. 4: Scheme 4, showing the synthesis of adenosine 5'-H-phosphonate.

Compound 135 can be prepared, for example, according to the scheme depicted in FIG. 4.

In some embodiments, the compositions of Formula I are compositions of Formula V:

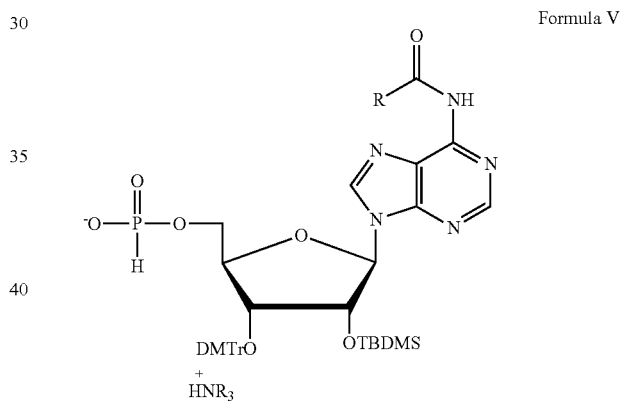

Formula V where R is phenyl or isobutyl. One non-limiting example of a composition of Formula V is compound 143:

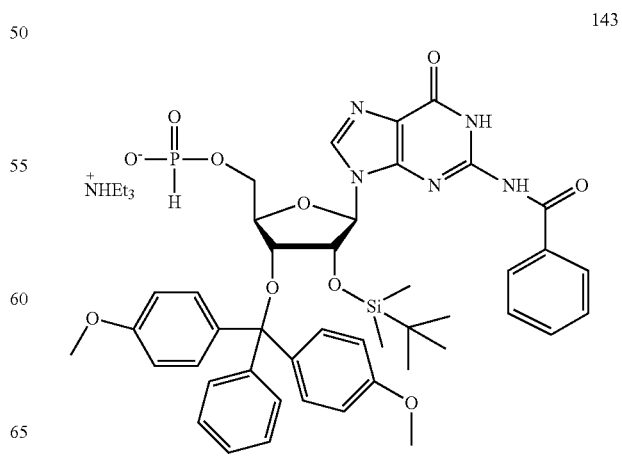

143

Figure 6:
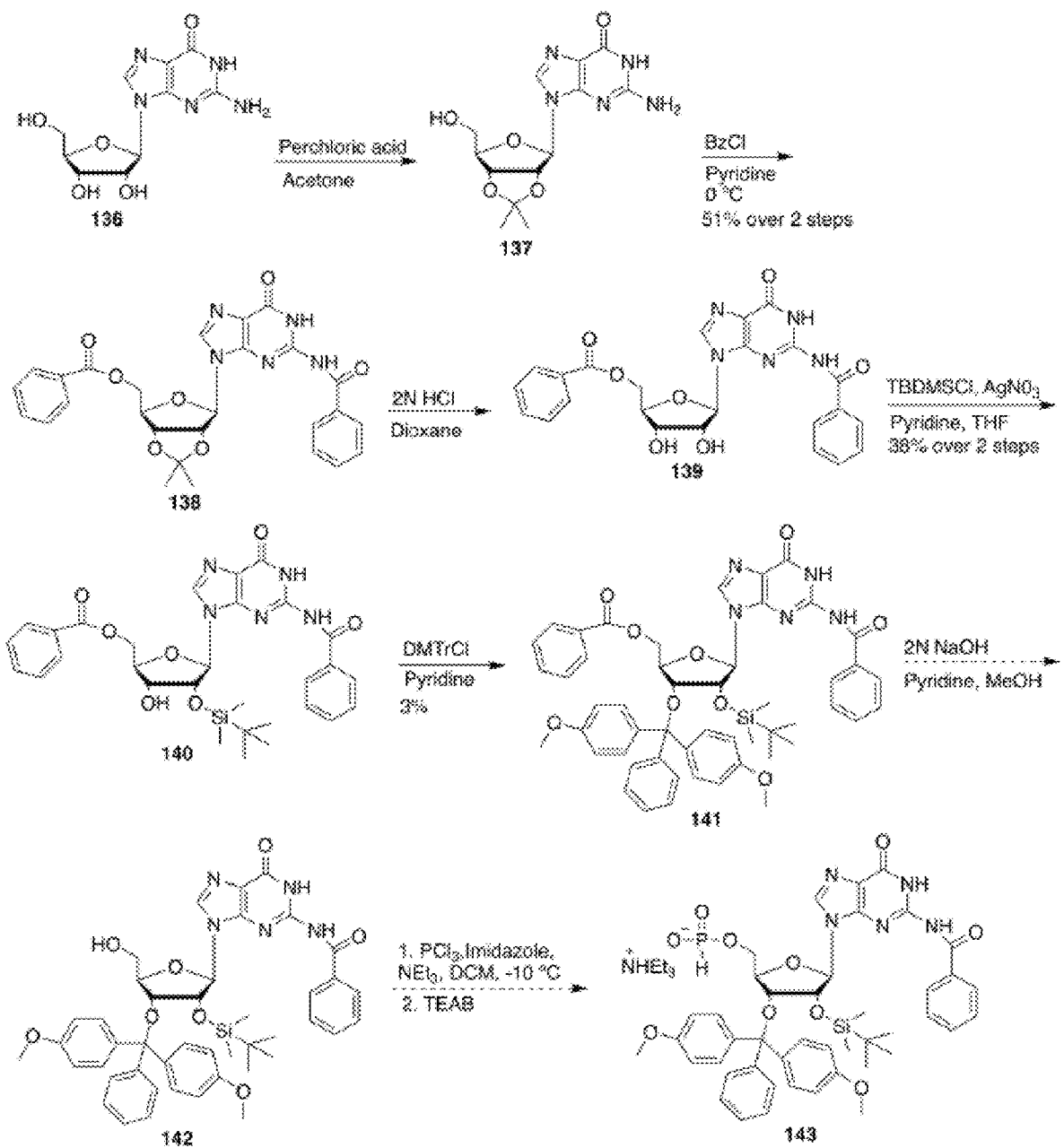
FIG. 6: Scheme 5, showing the synthesis of guanosine 5'-H-phosphonate using benzoyl protecting groups.

Compound 143 can be prepared, for example, according to the scheme depicted in FIG. 6.

Also provided is a method of making the 5'-H-phosphonates. FIGS. 2-4, 6-8 show synthetic routes for making 5'-H-phosphonates. A non-limiting example method for preparing the compounds of Formula I involves first protecting a nucleoside at the 2' position with a protecting group to form a 2'-protected nucleoside. This can be accomplished, for example, by reacting the nucleoside with a protecting group in acetone. Then, the 2'-protected nucleoside is protected at the 5' position to form a fully protected nucleoside. This can be accomplished, for example, by benzoylating the nucleoside with benzoyl chloride in pyridine. The fully protected nucleoside is then hydrolyzed in acid with heat to form a hydrolyzed protected nucleoside. The hydrolysis can be conducted in, for instance, 25% acetic acid at 100° C. for 1 hour. The hydrolyzed protected nucleoside is then silylated at the 2' position, followed by protected at the 3' position with a protecting group. The protected silylated nucleoside is then selectively deprotected at the 5' position to produce a 5' hydroxyl nucleoside. This can be accomplished by, for example, subjecting the protected silylated nucleoside to 2N NaOH in pyridine and methanol. The 5' hydroxyl nucleoside is then phosphonated to form a 5'-H-phosphonate. The phosphonation can be accomplished, for example, by reacting the protected silylated nucleoside with phosphorous trichloride ($PCl_3$), imidazole, and triethylamine in a suitable solvent (such as dichloromethane) and in the presence of tetraethylammonium borohydride (TEAB).

As noted above, the compounds of Formula I can be used in a method of synthesizing an oligonucleotide in the 5' to 3' direction. Thus, further provided is a method of oligonucleotide synthesis. Automated oligonucleotide synthesis is widely used to synthesize strands of DNA and RNA for various uses. The basis for which this works is the coupling of the phosphorous moiety of the added nucleotide with the free hydroxyl group of the extending strand of nucleotides. This process conventionally includes coupling, oxidation, and deprotection steps, which are repeated until the desired length is achieved. Automated RNA synthesis can be accomplished using a variety of building blocks, however the most commonly used are the phosphoramidites and H-phosphonates. Both utilize the same base protecting groups such as benzoyl and isobutyryl, and both use similar sugar protecting groups such as dimethoxytrityl for 5' protection and a tert-butyldimethylsilyl for 2' protection. The difference is in the phosphorus moiety at the 3' position, which both utilize P(III). Many phosphoramidites contain a bulky diisopropylamino group and require a cyanoethyl protecting group, while the H-phosphonate contains a phosphoryl functionality as well as a hydrogen atom attached to the phosphorous. Due to this difference, the automated synthesis using H-phosphonates is altered. H-phosphonates have a tetrahedral geometry like P(V) compounds and lack a pair of electrons, making them electrophilic. This makes H-phosphonates much more stable to oxidation compared to phosphoramidites, which require an oxidation step after each coupling cycle. Aside from this, the steps for the two processes may be similar. First, the dimethoxytrityl group is removed, giving a free 5' hydroxyl to couple with the added monomer, which is facilitated by an activator. After the condensation, there is a capping step to ensure no further reactivity. Finally, in the case of the phosphoramidite, there is the oxidation step that is repeated until the oligomer is of the desired length, then the final base and 2' deprotections, as well as the removal of the solid support, are performed.

Synthesis in the 5' to 3' direction allows for the introduction of a variety of 3' modifications such as ligands and chromophores to aid research in multiple fields. For example, this is applicable for RNA therapeutics by providing easy access to 3' modifications on the sense strand of siRNA, which should not interfere with recognition since antisense siRNA strands guide target recognition. Synthesis in the 5' to 3' direction also allows for more steric modifications on the sugar moiety, especially the 5' position when using an H-phosphonate.

There are numerous advantages to using H-phosphonate chemistries over those of phosphoramidites. Phosphoradmidites require an oxidation step after each coupling cycle, whereas in H-phosphonate chemistry only one oxidation step is required at the end of oligomer assembly. This cuts down the number of steps required in each cycle, as well as the cycle time. H-phosphonates are also more stable than phosphoramidites, and have the ability to be recovered after coupling. H-phosphonate chemistry also uses some of the same readily available reagents used in the phosphoramidite approach, and therefore does not require use of special reagents.

In the method of oligonucleotide synthesis, the oligonucleotide is formed from the 5' to 3' direction. This relies on the attachment of the initial nucleotide through its 5'-end to a polymer support. This method can be effectively executed through the assembly of nucleoside monomers which contain an H-phosphonate moiety at the 5'-end with appropriate protection at the 3'-end. Due to the small size of the H-phosphonate group, this methodology is uniquely suited for the incorporation of modified nucleosides containing sterically demanding modifications at the site of linkage. The oligonucleotides synthesized using this method can also be used in any applications which employ synthetic nucleic acid polymers.

The method takes advantage of existing chemistry for the synthesis of automated synthesis of oligonucleotides employing efficient means for the formation of covalent bonds between the polymer bound substrate and an incoming nucleotide in a sequence specific manner Monomers are formed with base protecting groups orthogonal to the overall chemistry.

Monomers described herein have been designed to be efficiently incorporated into a growing oligonucleotide chain. Bases (adenine, guanine, thymine, cytidine, uracil, etc.), the nitrogen containing heterocycles contained in each nucleoside, are appropriately protected with groups which can be used under standard conditions which have been shown not to damage the RNA backbone or the unprotected bases. These groups include, but are not limited to, benzoyl and isobutyryl. The method is suitable for synthesizing ribonucleotides, meaning that the sugar attached to the base is ribose or a modification thereof. However, other applications are entirely possible and encompassed within the present disclosure.

Figure 9:
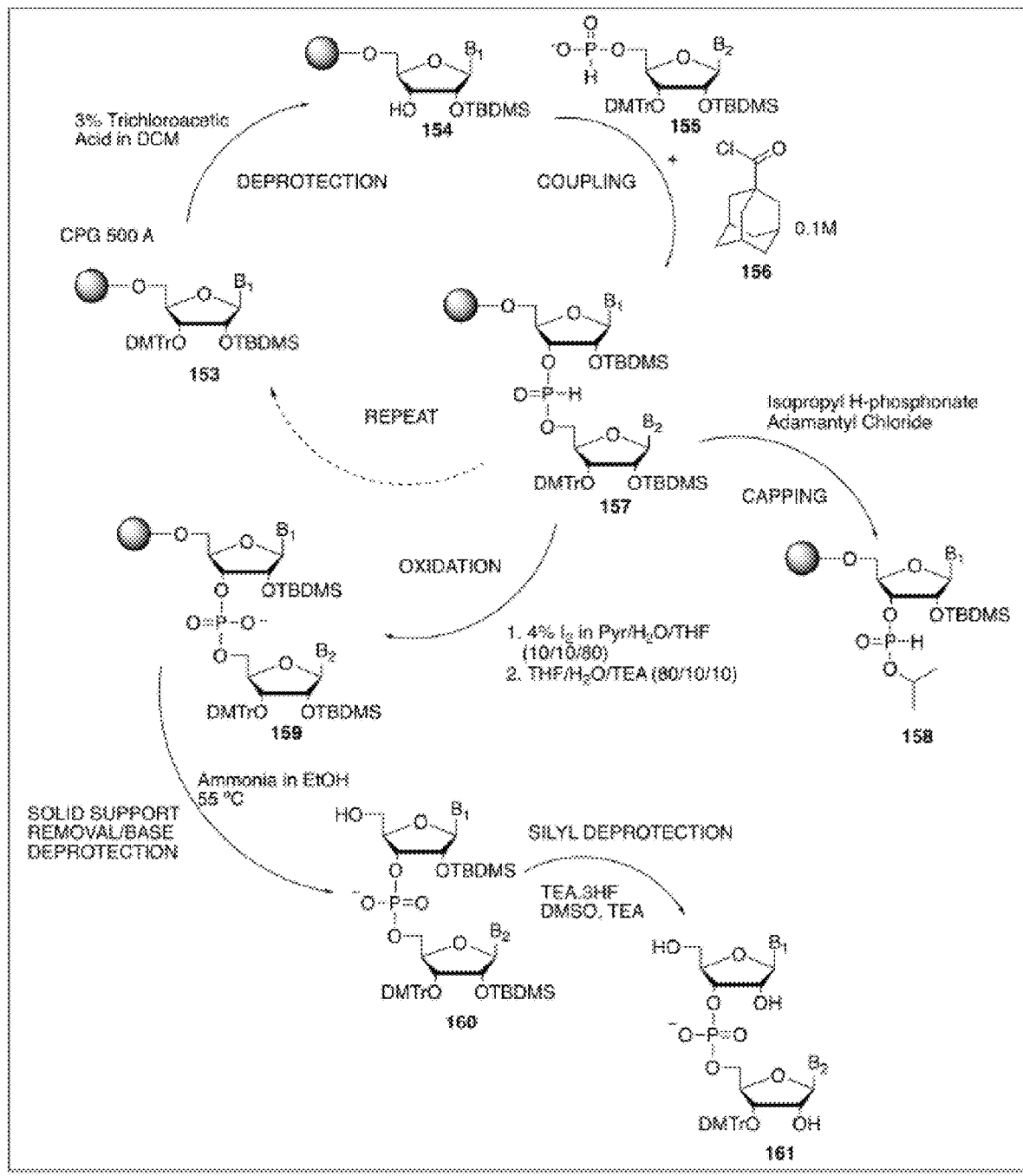
FIG. 9: Scheme 8, depicting an automated oligonucleotide synthesis method.
Figure 14:
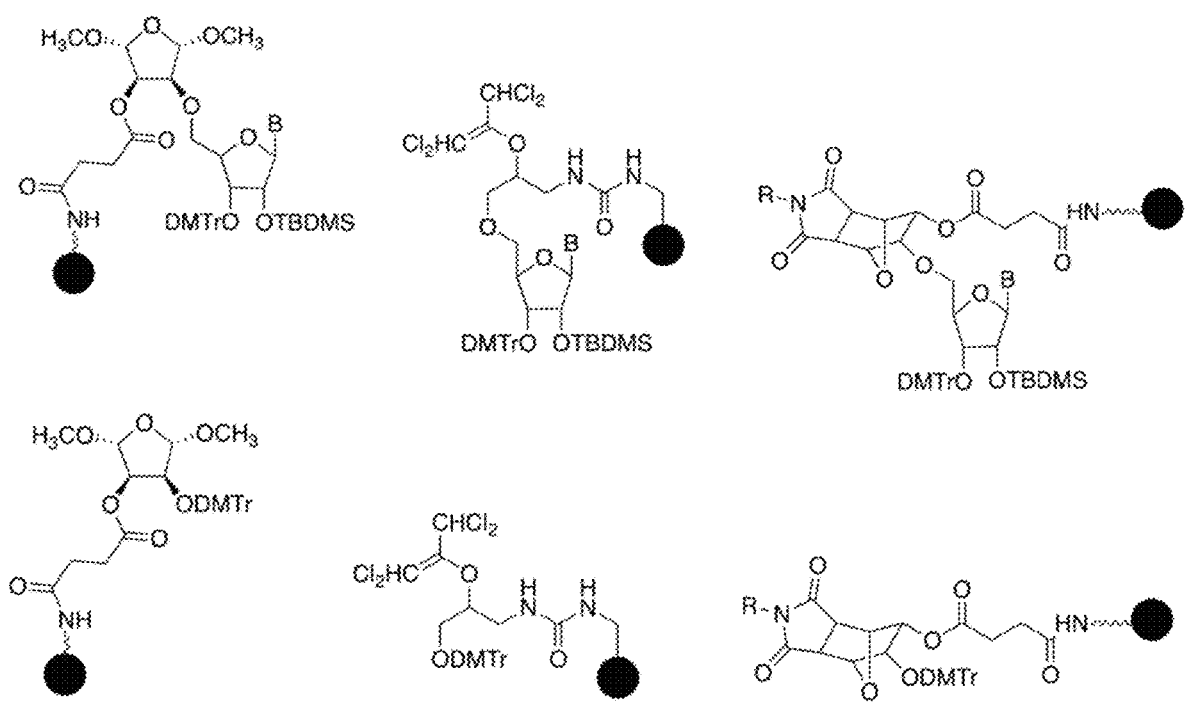
FIG. 14: Non-limiting examples of commercially available linkers bound to supports.

As an example method, automated oligonucleotide synthesis can be achieved in accordance with the present disclosure as follows: A 3'-DMTr (dimethoxytrityl) protected nucleoside is linked through a suitable linker to a support. FIG. 14 shows non-limiting examples of commercially available linkers bound to supports. The support is then treated with a halogenated carboxylic acid in dichlormethane to free the 3' hydroxyl of the support-bound nucleoside. A second nucleotide is added as a 3'-dimethoxytrityl-5'-H-phosphonate salt and coupling is initiated through activation using a bulky carboxylic acid chloride. The resulting H-phosphonate linkage can be oxidized using I₂/H₂O/pyridine/THF to the phosphate directly after monomer incorporation, or this step can be left until the entire oligomer is assembled. Unreacted 3' ends are capped by esterification with the excess acid chloride left after coupling or use of acetic anhydride/pyridine. These capping groups are amenable to removal under standard oligonucleotide purification techniques to facilitate purification of the final substrate. The process of deprotection, coupling, capping, and oxidation is repeated as appropriate to provide the desired sequence. An example of this method is illustrated in FIG. 9.

The method described herein can be used to prepare a wide variety of oligonucleotides, including RNA or DNA molecules. The synthesized oligonucleotides can then be used in, for instance, PCR, sequencing, microarrays, Southern blots, ASO analysis, fluorescent in situ hybridization, or artificial gene synthesis.

Suitable protection for the compounds of Formula I in the oligonucleotide synthesis method may include benzoyl protection, pentafluorophenyl benzoate protection, DMT protection, tritylation, phosphitylation, silylation, benzoylation, or transient protection. Non-limiting example protecting groups are N(6)-benzoyl, N(2)-isobutyryl, N(4)-benzoyl, N(2)-dimethylformamidyl, N(6)-phenoxyacetyl, N(2)-isopropyl phenoxyacetyl, or N(2)-acetyl.

Any suitable solid support may be utilized in the oligonucleotide synthesis method. A solid support is an insoluble particle, typically 50-200 microns in diameter, to which the oligonucleotide is bound during synthesis. Suitable solid supports include, but are not limited to, controlled pore glass or highly cross-linked polystyrene resins. A linker is attached at the 5' end of the oligonucleotide to the solid support. Suitable linkers include, but are not limited to, succinyl linkers. Succinyl linkers can be cleaved by treatment with ammonium hydroxide at room temperature.

Oxidation in the oligonucleotide synthesis method can be accomplished using, for instance, iodine in the presence of water and pyridine. However, other methods of oxidation are possible and encompassed within the scope of the present disclosure. As noted above, oxidation may be conducted in a single step at the end of the process, or may be conducted after each monomer is incorporated.

To accomplish deprotection of the oligonucleotide, the oligonucleotide may be heated to remove the protecting groups from the heterocyclic bases and phosphonates. The aqueous solution can then be removed by evaporation, leaving the oligonucleotide ready for purification. Detritylation can be accomplished, for example, with trichloroacetic acid in dichloromethane.

It is further envisioned that the compositions and methods described herein can be embodied in the form of a kit or kits. A non-limiting example of such a kit is a kit for conducting an oligonucleotide synthesis, the kit comprising a 5'-H-phosphonate and a support-bound nucleoside in separate containers, where the containers may or may not be present in a combined configuration. Many other kits are possible, such as kits that further include one or more of a halogenated carboxylic acid, an esterification agent, an oxidizing agent, or a protecting group. The kits may further include instructions for using the components of the kit to practice the subject methods. The instructions for practicing the subject methods are generally recorded on a suitable recording medium. For example, the instructions may be present in the kits as a package insert or in the labeling of the container of the kit or components thereof. In other embodiments, the instructions are present as an electronic storage data file present on a suitable computer readable storage medium, such as a flash drive or CD-ROM. In other embodiments, the actual instructions are not present in the kit, but means for obtaining the instructions from a remote source, such as via the internet, are provided. An example of this embodiment is a kit that includes a web address where the instructions can be viewed and/or from which the instructions can be downloaded. As with the instructions, this means for obtaining the instructions is recorded on a suitable substrate.

EXAMPLES

An automated RNA synthesis method in the 5' to 3' direction using 5'-H-phosphonates was developed. These examples include the synthesis of the building blocks for the automated synthesis in the 5' to 3' direction using 5'-H-phosphonates.

5' Uridinyl Radical Precursor H-Phosphonate Synthesis 96 was derivatized to contain a 5'-H-phosphonate with the appropriate protecting groups for RNA synthesis. The synthesis is shown in Scheme 1 (FIG. 1). First, 96 was protected with a dimethoxytrityl group on the 3' hydroxyl using DMTrCl and DMAP in pyridine. Compound 93 was then acylated at the 2' hydroxyl using Ac₂O (acetic anhydride), NEt₃, and a catalytic amount of DMAP in DCM. This was then subjected to H-phosphonate addition conditions using PCl₃ and NEt₃, then TEAB. Compound 113 was confirmed by HRMS, however the $^{31}$P NMR clearly shows that it was oxidized to monophosphate 94. Though H-phosphonates are more stable to oxidation than their phosphoramidite counterparts, it can still occur. The purification of compound 113 left it too exposed. It may be used without further purification to prevent this issue.

H-Phosphonate Monomer Synthesis

Overview of 5'-H-Phosphonate Synthesis

An automated RNA synthesis technique based on the assembly of the oligomer in the 5' to 3' direction was designed using 5'-H-phosphonates. This includes the synthesis of the four RNA building blocks, uridine, cytidine, adenosine, and guanosine 5'-H-phosphonates.

Uridine 5'-H-Phosphonate Synthesis

Figure 2:
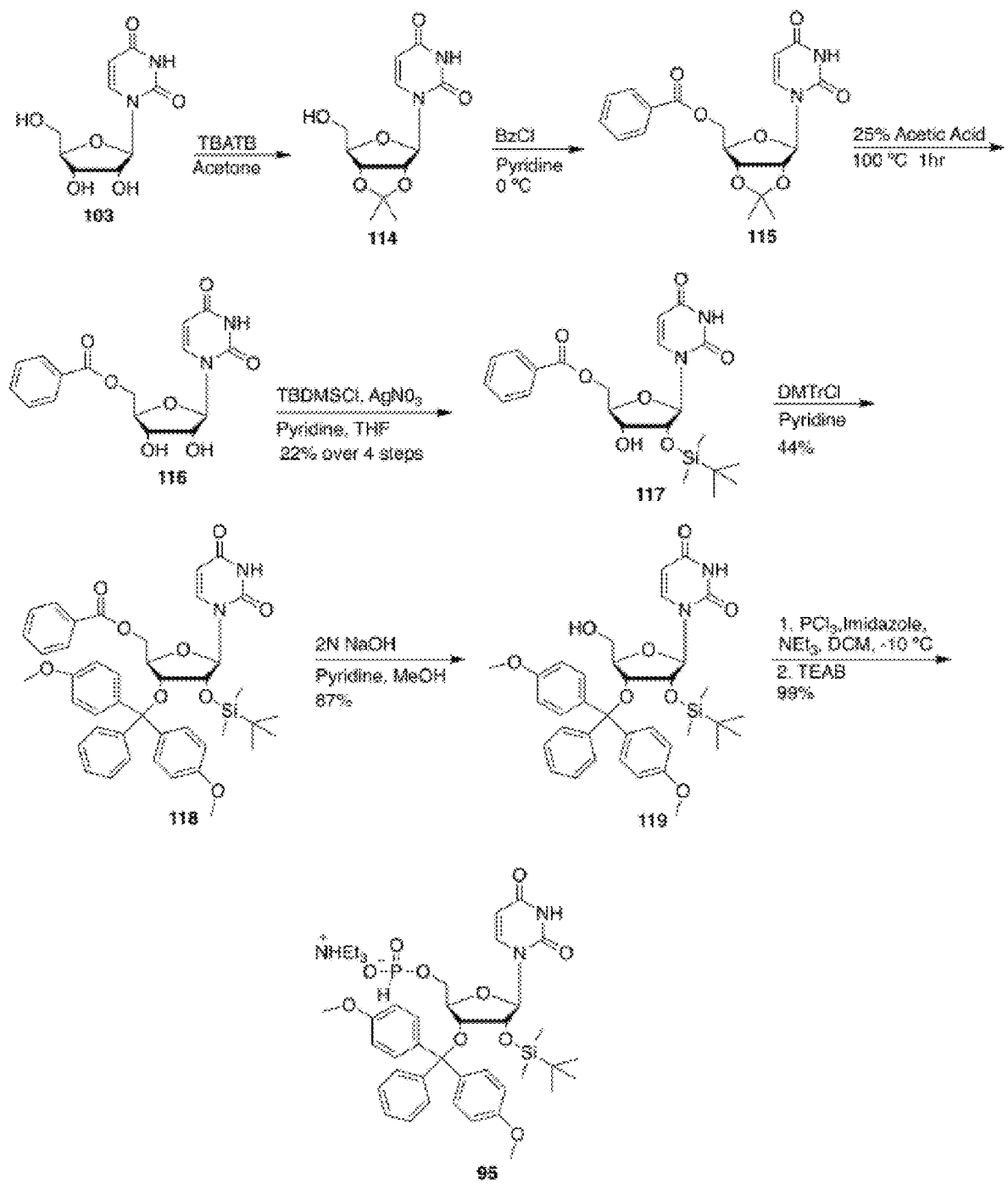
FIG. 2: Scheme 2, showing the synthesis of uridine 5'-H-phosphonate.

The synthesis of 95 can be seen in Scheme 2 (FIG. 2). First, uridine was protected using a catalytic amount of tetrabutylammonium tribromide (TBATB) in acetone to give 114. This was benzoylated at the 5' position using benzoyl chloride (BzCl) in pyridine to afford 115. Fully protected 115 then underwent acidic hydrolysis using 25% acetic acid and heat to give 116. Compound 116 was selectively silylated at the 2' position using tert-butyldimethylsilyl chloride and silver nitrate (AgNO₃) in a mixture of pyridine and tetrahydrofuran. Compound 117 was then protected using dimethoxytrityl chloride in pyridine to give 118, which was finally selectively deprotected using 2N sodium hydroxide (NaOH) in pyridine and methanol to give 5' hydroxyl 119. The addition of the H-phosphonate was completed using phosphorous trichloride, imidazole, and triethylamine in dichloromethane.

Cytidine 5'-H-Phosphonate Synthesis

The synthesis of 127 can be seen in Scheme 3 (FIG. 3). First, cytidine was protected using a catalytic amount of perchloric acid in acetone to give 121. This was benzoylated at the 5' position, as well as on the exocyclic amine, using benzoyl chloride (BzCl) in pyridine to afford 122. These first two steps had high crude yields and likely are not part of the reason for the low combined yield. Fully protected 122 then underwent acidic hydrolysis using dilute hydrochloric acid (HCl) in dioxane to give 123. This gave a crude yield of approximately 50%. In the workup, the crude product was redissolved in EA and THF, though there were solubility issues. Even when DCM and MeOH are added to help this, it is possible that in the aqueous washes some product is lost. This acid hydrolysis has also been shown to be problematic with the guanosine and adenosine nucleosides, possibly causing some compound degradation. To further investigate this, 122 should be purified before the acid hydrolysis. Compound 123 was selectively silylated at the 2' position using tert-butyldimethylsilyl chloride and silver nitrate ($AgNO_3$) in a mixture of pyridine and tetrahydrofuran. The selective protection gives preference to the formation of the desired 2' hydroxyl, however it also gives rise to the protected 3' hydroxyl and bis-protected compounds. Combined, these steps delivered 124 in a very low yield. In part, this was due to the lack of purification in between any of these reactions. Compound 122 should be purified before moving forward, and, most importantly, compound 123 should be very carefully purified so as to give a pure compound going into the selective protection. Another possibility is to deploy a scheme similar to what was adopted with guanosine where there is a transient protection of the three hydroxyl groups to start with a base protected nucleoside, removing the need to perform the isopropylidene removal. Compound 124 was then protected using dimethoxytrityl chloride in pyridine to give 125 in a crude yield of 84%, after which an attempt to selectively deprotect by using 2N sodium hydroxide (NaOH) in pyridine and methanol failed. Compound 125 should therefore be purified before moving forward to ensure there is one pure product to test the reaction with.

Adenosine 5'-H-Phosphonate Synthesis

The synthesis approach for 135 can be seen in Scheme 4 (FIG. 4). First, adenosine was protected using a catalytic amount of perchloric acid in acetone to give 129. This was benzoylated at the 5' position, as well as on the exocyclic amine, using benzoyl chloride (BzCl) in pyridine to afford 130. Here, it is also possible to form a compound with two Bz protecting groups on the exocyclic amine. It was observed that this had started to form before the starting material was fully consumed, so the reaction was stopped. Varying conditions may be altered to optimize this procedure, including by moving forward with an adenosine compound obtaining three Bz protecting groups. Fully protected 130 then underwent acidic hydrolysis using dilute hydrochloric acid in dioxane to give 131. Again, this saw low crude yields. Compound 131 was selectively silylated at the 2' position using tert-butyldimethylsilyl chloride and silver nitrate ($AgNO_3$) in a mixture of pyridine and tetrahydrofuran. Compound 132 was then protected using dimethoxytrityl chloride in pyridine to give 133 with a crude yield of 88%, which was pushed forward to attempt the selective deprotection using 2N sodium hydroxide (NaOH) in pyridine and methanol which failed. Compound 133 should be purified before going forward to ensure a single, pure product to test the reaction with. As stated before, the scheme could be modified as in the case of guanosine to remove the need to use an isopropylidene protecting group on the 2' and 3' hydroxyls, which should reduce the number of steps used and increase the overall yields.

Guanosine 5'-H-Phosphonate Synthesis

Figure 5:
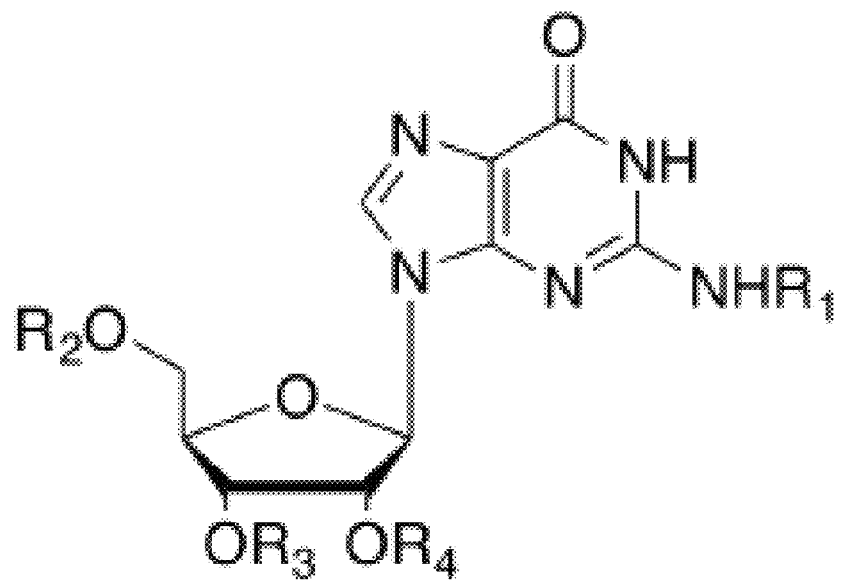
FIG. 5: Non-limiting example guanosine protecting groups.

An appropriately protected guanosine is required for RNA synthesis and multiple candidates were investigated in an attempt to achieve this (FIG. 5). The protecting groups could vary for the base, however the isobutyryl (Ibu) group is commonly used for guanosine, likely due to its easier removal during automated synthesis. For the 5' protecting group, the benzoyl (Bz) group aided greatly in compound solubility. First, the same approach as used in the other nucleosides was attempted, seen in Scheme 5, (FIG. 6). Guanosine was protected using a catalytic amount of perchloric acid in acetone to give 137. This was benzoylated at the 5' position, as well as on the exocyclic amine, using benzoyl chloride (BzCl) in pyridine to afford 138. Fully protected 138 then underwent acidic hydrolysis using dilute hydrochloric acid in dioxane to give 139. This reaction was performed multiple times, and the product would sometimes degrade during the reaction. However, more success was observed during faster acidic hydrolysis prompted by heat. Compound 139 was selectively silylated at the 2' position using tert-butyldimethylsilylchloride and silver nitrate in a mixture of pyridine and tetrahydrofuran. This reaction was more successful when the previous reaction was purified or the product was washed with a saturated sodium bicarbonate solution and brine, however 139 does have some solubility issues. Under these reaction conditions, the compound was also prone to decompose via base release. Compound 140 was then protected using dimethoxytrityl chloride in pyridine to give 141. The selective debenzylation was attempted and appeared to work, however the compound degraded shortly after the purification.

Figure 7:
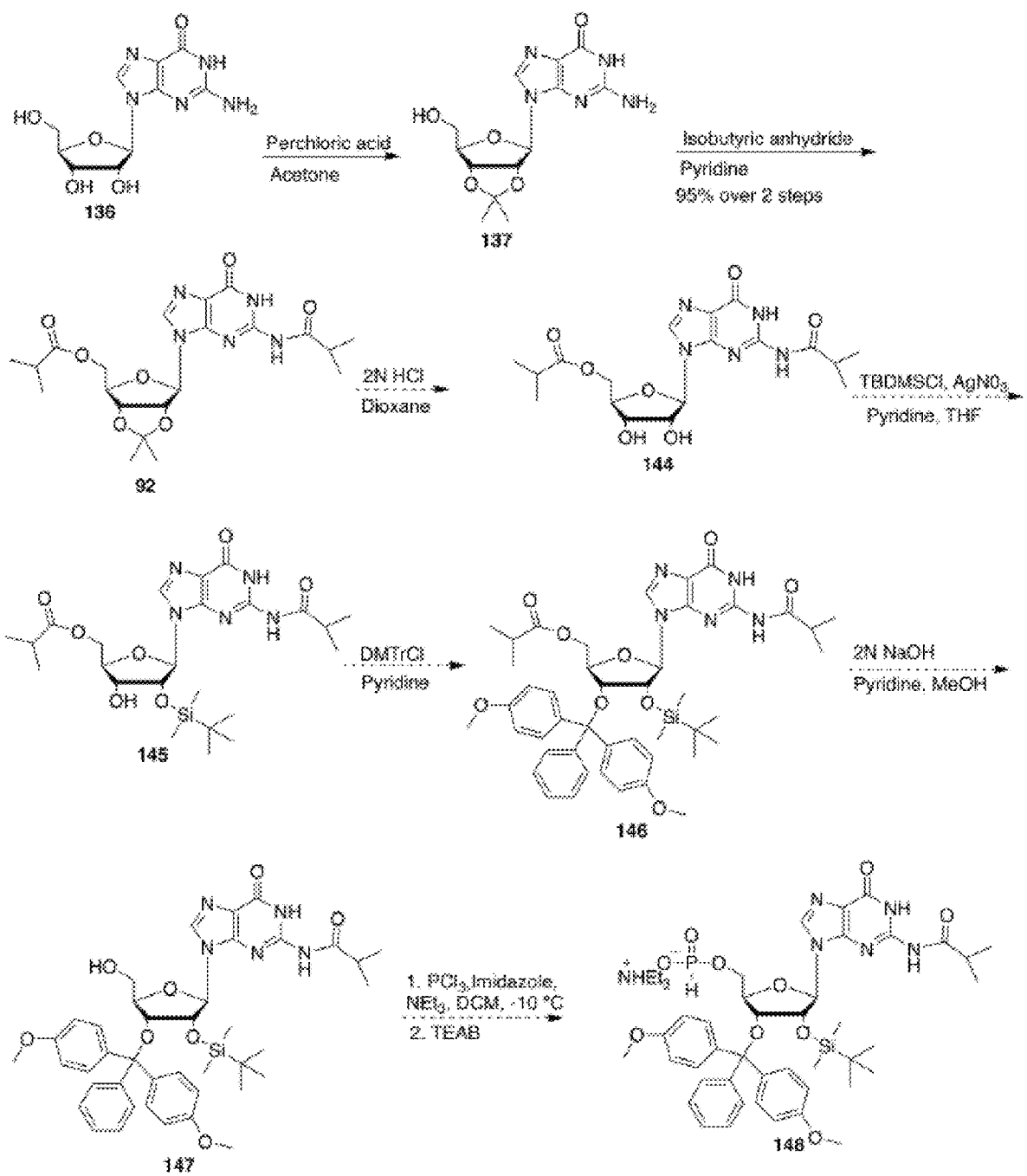
FIG. 7: Scheme 6, showing the synthesis of guanosine 5'-H-phosphonate using isobutyryl protecting groups.
Figure 8:
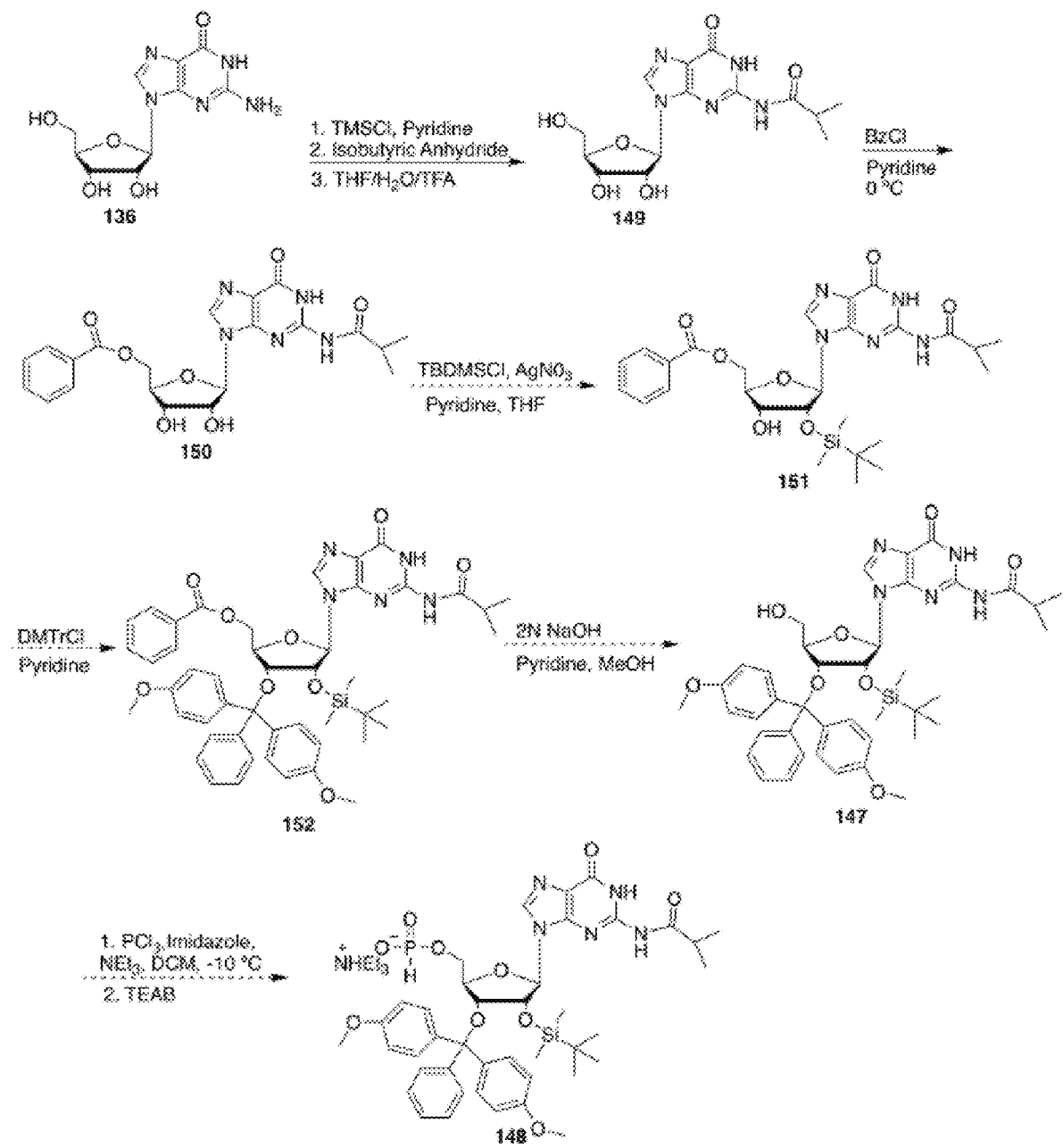
FIG. 8: Scheme 7, showing the synthesis of guanosine 5'-H-phosphonate using a combination of isobutyryl and benzoyl protecting groups.

Second, a similar approach as was used in the other nucleosides was attempted using the isobutyryl protecting groups, a more commonly used base protecting group for guanosine, seen in Scheme 6 (FIG. 7). Guanosine was protected using a catalytic amount of perchloric acid in acetone to give 137. This was protected at the 5' position, as well as on the exocyclic amine, with Ibu using isobutyric anhydride in pyridine to afford 92. Fully protected 92 underwent acidic hydrolysis using dilute hydrochloric acid in dioxane with the attempt of forming 139. However, under these conditions, the 5' isobutyryl group was consistently lost as well.

Finally, the approach outlined in Scheme 7 (FIG. 8) was adopted. This removed the need to use the isopropylidene altogether, as well as utilized the more common Ibu protecting group on the base and the Bz group beneficial for solubility on the 5' position. The hydroxyl groups of guanosine were exposed to transient protection using TMSCl (trimethylsilyl chloride) in pyridine, followed by the addition of isobutyric anhydride to protect the base and then the addition of water and THF with TFA (trifluoroacetic acid) to secure the removal of the TMS groups to afford 149. Adding methanol may be more beneficial than water yielding more methyl isobutyrate, which has a lower boiling point than isobutyric acid and may be easier to remove. This also may allow for the purification of this compound, though it may have solubility issues.

Conclusions

The H-phosphonate C5'-uridinyl radical precursor was synthesized for incorporation into strands of RNA. Some of the C5'-uridinyl radical precursor degraded to form phosphate 94.

Materials, Methods, and Equipment

All reactions were carried out under laboratory conditions using argon or nitrogen in clean, oven-dried flask unless otherwise stated. All chemicals and reagents were obtained commercially and used without further purification unless otherwise stated. New compounds were characterized using Nuclear Magnetic Resonance (NMR) and High Resolution Mass Spectrometry (HRMS). $^1$H NMR were obtained on a VXR 400, Inova 600, or Avance 600 NMR using $CDCl_3$ or MeOH-$d_4$. $^{13}$C NMR were obtained on an Avance 600 NMR using $CDCl_3$ or MeOH-$d_4$. $^{31}$P NMR were obtained on a VXR 400 using $CDCl_3$. HRMS were obtained from an electrospray ionization (ESI)-quadrupole time-of-flight (Q-TOF) mass spectrometer. Low Resolution Mass Spectrometry were obtained using either an Esquire-electrospray ionization mass spectrometer or a Shimadzu LCMS 2020. High-Performance Liquid Chromatography (HPLC) was completed using either a Dionex Ultimate 3000 equipped with a variable wavelength detector or a Shimadzu LC 20-AT with a UV detector. High-Performance Liquid Chromatography-Mass Spectrometry (LCMS) was accomplished using a Shimadzu LC 20-AT connected to a Shimadzu LCMS 2020. Purification of compounds was done using either a manual column with silica or alumina or a Biotage SP4 automated chromatography system using Biotage SNAP pre-packaged silica columns. Thin Layer Chromatography (TLC) was carried out using silica gel 60 F254 aluminum backed plates and visualized by UV light at 254 nm followed by staining and burning using anisaldehyde dip. Photolysis reactions were carried out using a Thermo Oriel with a 500 W mercury lamp and cut-off filter for wavelengths greater or equal to 320 nm, a Thermo Haake K20 cooling system and a Varian SPV Cary single cell peltier accessories. Other equipment used include a solvent purification system (Innovative Technology PS-MD-2 Pure Solvent System), rotary evaporators (Heidolph Collegiate Brinkmann rotovap), high vacuum pump (Edwards RV3), speed vacuum (Thermo electron savant DNA120), micro centrifuge (Thermo Sorvall Legend Micro 21), vortex mixer (Fisher Scientific), Milli-Q water purification system, pH meter (Fisher Accumet Basic AB15), and pipettes (Eppendorf Series 2100).

Synthesis of Compounds

Synthesis of ((3aR,4R,6R,6aR)-6-(2-isobutyramido-6-oxo-1,6-dihydro-9H-purin-9-yl)-2,2-dimethyltetrahydrofuro[3,4-d][1,3]dioxol-4-yl)methyl isobutyrate 92

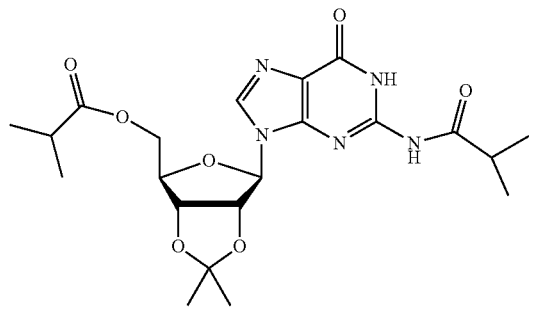

Figure 10A:
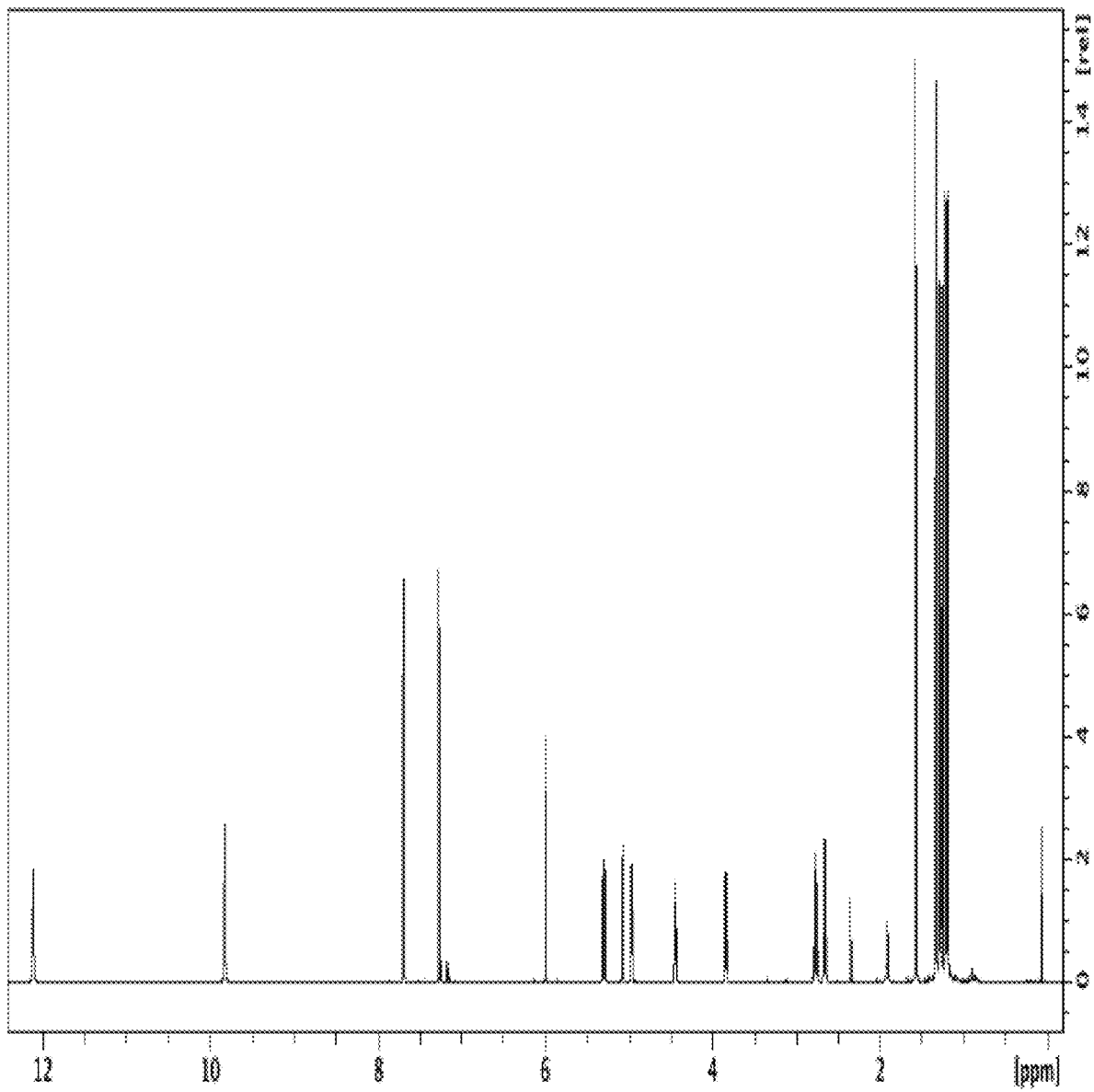
FIGS. 10A-10C: $^1$H NMR (FIG. 10A), $^{13}$C NMR (FIG. 10B), and HRMS (FIG. 10C) spectra of 92.
Figure 10B:
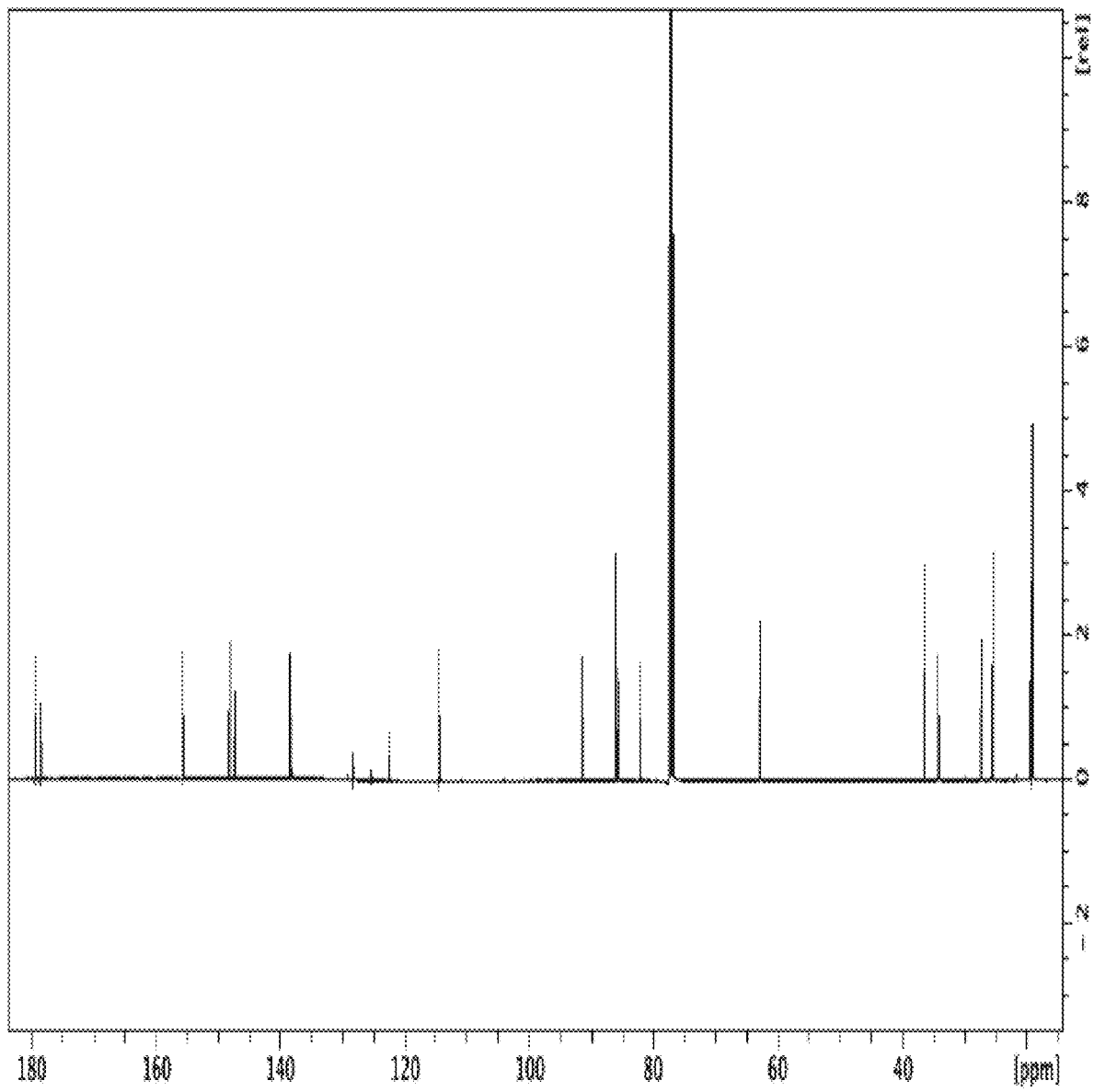
Figure 10C:
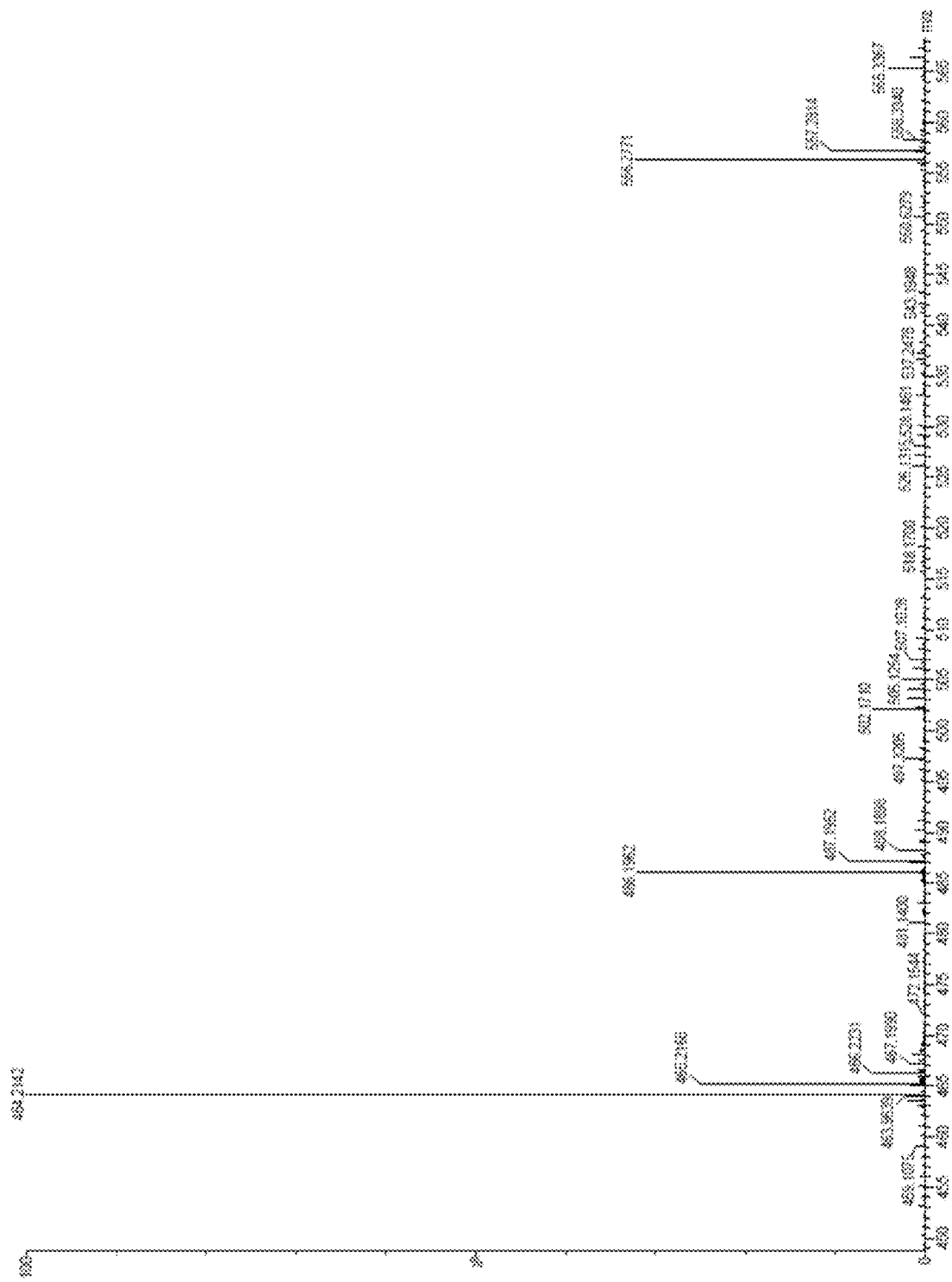

5.10 g (18.0 mmol) guanosine was dissolved in 245 mL of acetone and then 3.5 mL of perchloric acid was added dropwise while stirring. After 24 hours, the mixture was submerged in an ice bath and 3.0 mL of ammonium hydroxide was added dropwise. The media was filtered and the collected precipitate was washed with cold acetone to afford a white solid. The compound was coevaporated with toluene then dissolved in 210 mL of pyridine and then 25 mL of isobutyric anhydride were added slowly while stirring. After 25 hours, the reaction was quenched with 25 mL of water and concentrated. The compound was purified on a silica column using an eluent of 1% to 10% methanol (MeOH) in dichloromethane (DCM). 95% yield. $^1$H NMR (600 Mz, CDCl$_3$) δ 12.12 (1H, s), 7.69 (1H, s), 5.99 (1H, d, J=1.3), 5.30 (1H, dd, J=11.1, 9.5), 5.07 (1H, dd, J=6.2, 1.3), 4.96 (1H, dd, J=6.5, 3.3), 4.44 (1H, m), 3.83, (1H, dd, J=11.2, 5.8), 2.77 (1H, sep, J=7.1), 2.65 (1H, sep, J=7.1), 1.91 (1H, s), 1.57 (3H, s), 1.32 (3H, s), 1.29 (3H, d, J=6.9), 1.26 (3H, d, J=6.9), 1.21 (3H, d, J=7.1), 1.19 (3H, d, J=7.0). $^{13}$C NMR (600 Mz, CDCl$_3$) δ 179.37, 178.62, 155.64, 148.14, 147.25, 138.43, 122.54, 114.47, 91.49, 86.21, 85.70, 82.27, 62.85, 36.56, 34.28, 27.28, 25.53, 19.36, 19.18, 19.05, 19.02. HRMS [M+H]$^+$ calculated for C$_{21}$H$_{29}$N$_5$O$_7$ 464.2145. Found 464.2142. FIG. 10A shows the $^1$H NMR spectrum of 92, FIG. 10B shows the $^{13}$C NMR spectrum, and FIG. 10C shows the HRMS of 92.

Synthesis of 1-((2R,3R,4S,5R)-4-(bis(4-methoxyphenyl)(phenyl)methoxy)-3-hydroxy-5-(1-hydroxy-3,3-dimethyl-2-oxobutyl)tetrahydrofuran-2-yl)pyrimidine-2,4(1H,3H)-dione 93

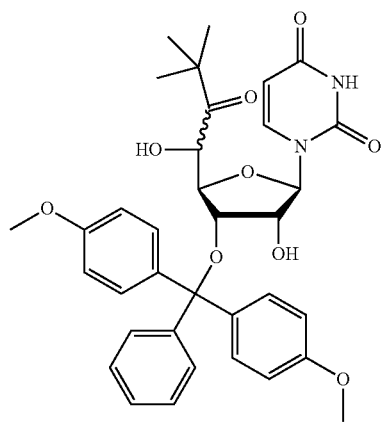

Figure 11A:
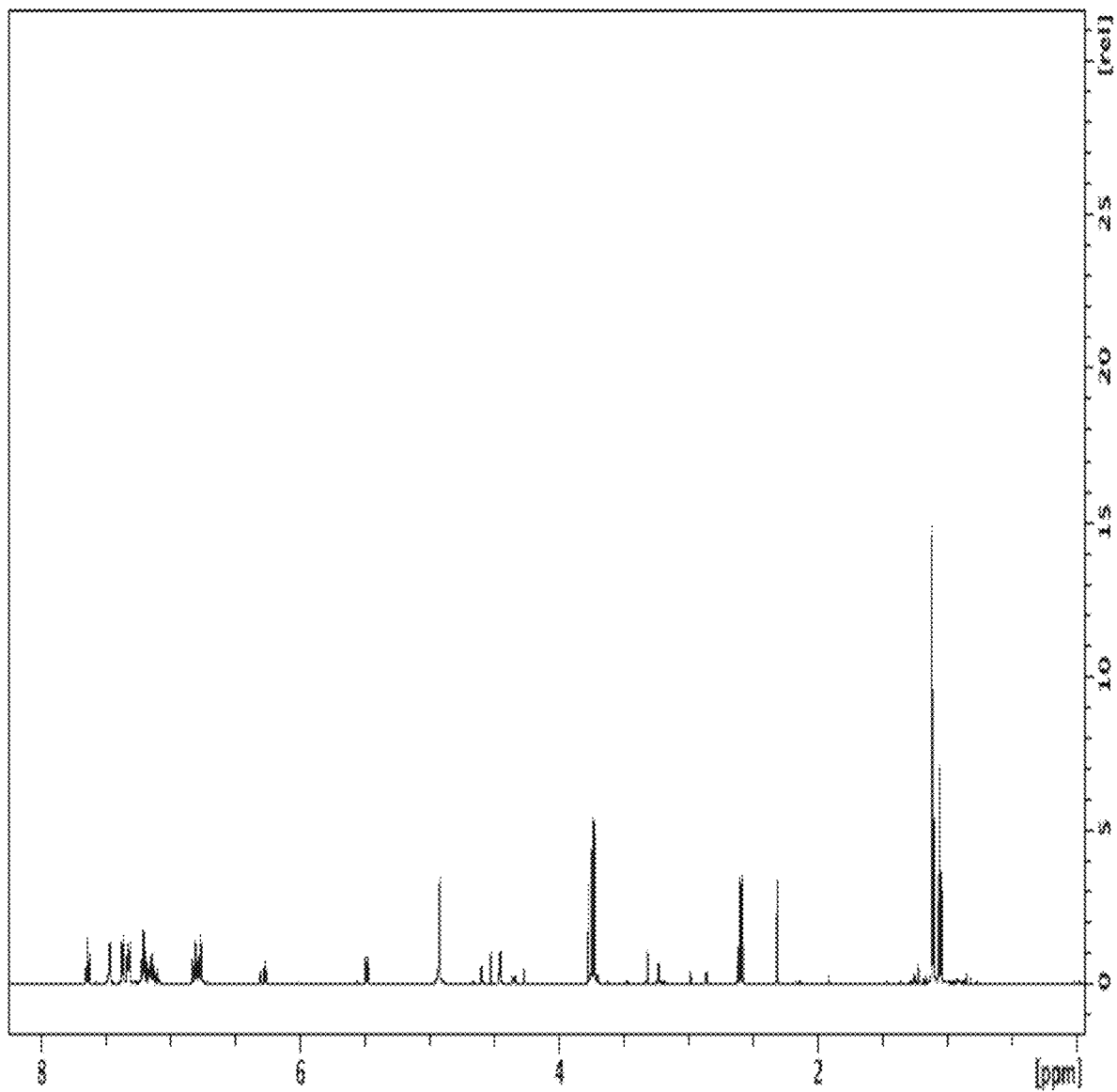
FIGS. 11A-11C: $^1$H NMR (FIG. 11A), $^{13}$C NMR (FIG. 11B), and HRMS (FIG. 11C) spectra of 93.
Figure 11B:
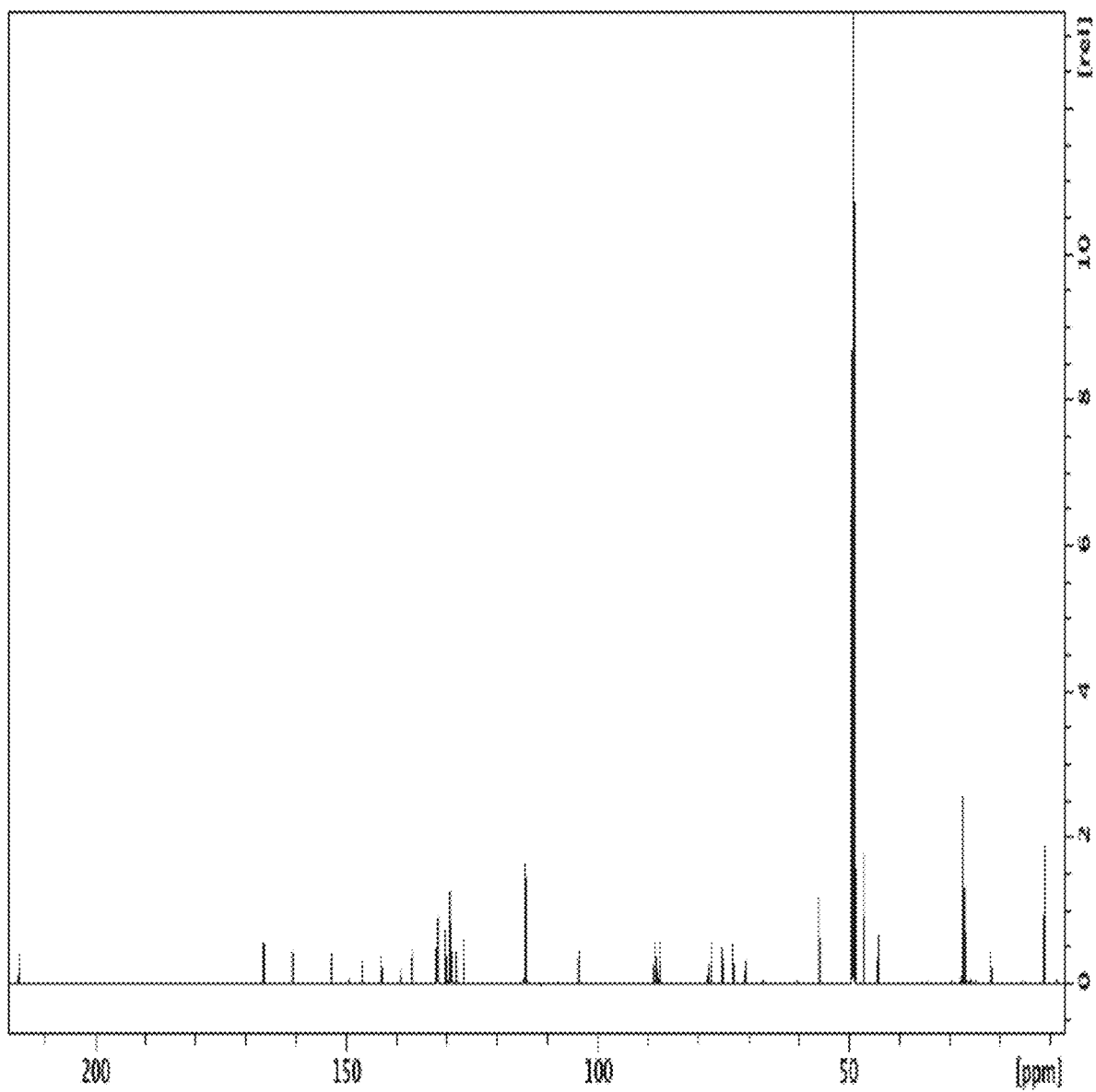
Figure 11C:
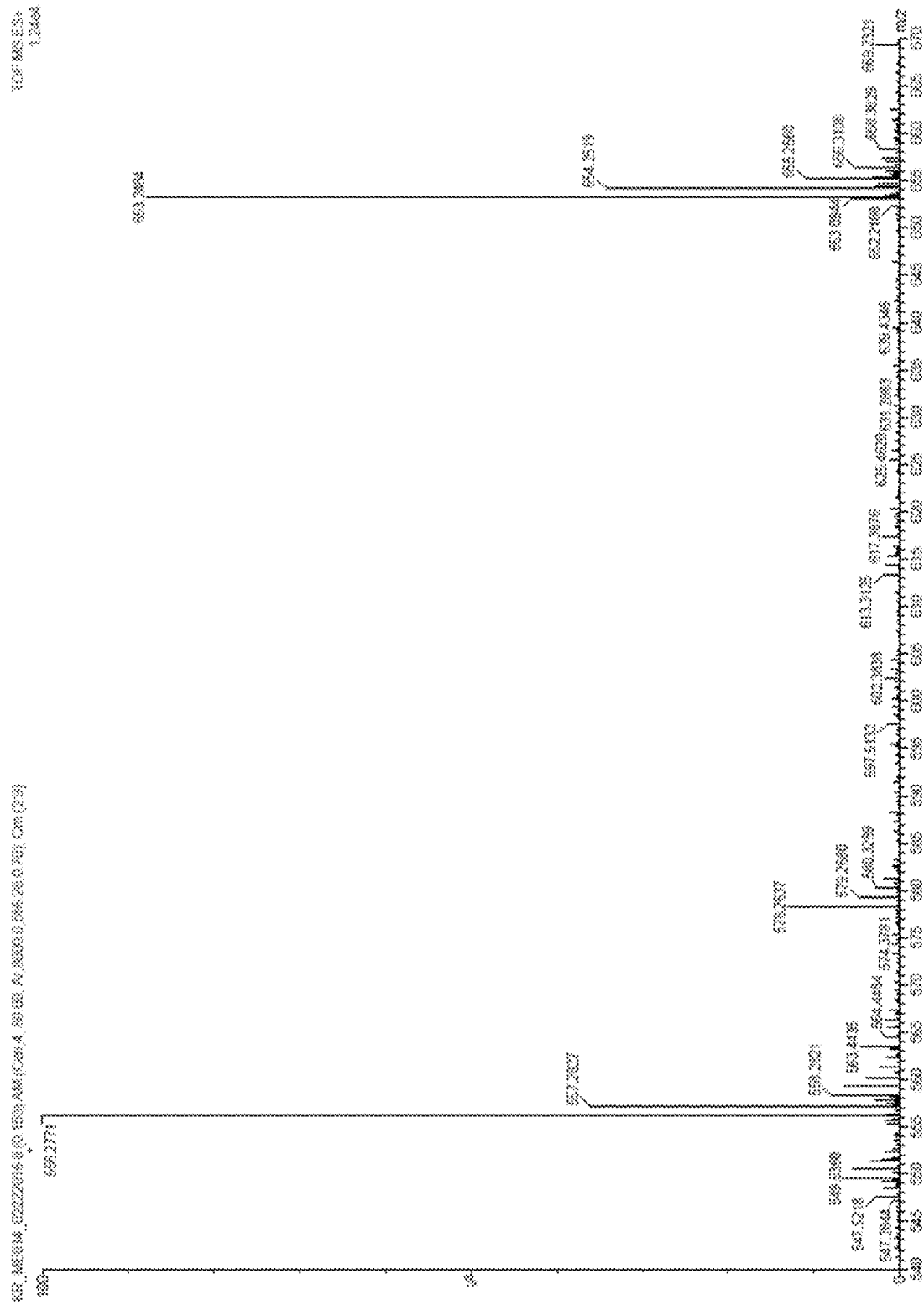

0.54 g (1.64 mmol) 96 was dissolved in 8 mL of pyridine then 0.65 g (1.92 mmol) dimethoxytrityl chloride (DMTrCl) was added. The reaction was stirred at room temperature. After 74 hours, an additional 0.10 g (0.30 mmol) dimethoxytrityl chloride and 0.02 g (0.16 mmol) DMAP (4-dimethylaminopyridine) were added to the solution. The reaction was chilled in an ice bath and quenched with 0.2 mL of methanol after 115 hours then concentrated. The compound was purified on a silica column using an eluent of 50% to 60% ethyl acetate (EA) in hexane with 5% triethylamine (NEt$_3$). 57% yield. $^1$H NMR (600 Mz, MeOH-d$_4$) δ 7.65 (1H, d, J=8.0), 7.63 (1H, d, J=8.0), 7.47 (2H, d, J=8.0), 7.47 (2H, d, J=8.0), 7.37 (2H, d, J=8.9), 7.37 (2H, d, J=8.5), 7.33 (2H, d, J=8.9), 7.32 (2H, d, J=8.9), 7.21 (3H, t, J=7.5), 7.20 (3H, t, J=8.5), 6.82 (2H, d, J=9.1), 6.80 (2H, d, J=8.8), 6.77 (2H, d, J=8.1), 6.76 (2H, d, J=8.8), 6.31 (1H, d, J=7.8), 6.27 (1H, d, J=7.8), 5.49 (1H, d, J=8.2), 5.48 (1H, d, J=8.2), 4.59 (1H, d, J=2.9), 4.52 (1H, d, J=2.2), 4.46 (1H, dd, J=7.9, 4.6), 4.45 (1H, d, J=2.1), 4.34 (1H, dd, J=7.5, 4.7), 4.27 (1H, d, J=2.5), 3.77 (3H, s), 3.74 (3H, s), 3.74 (3H, s), 3.72 (3H, s), 3.23 (1H, d, J=4.7), 2.86 (1H, d, J=4.7), 1.12 (9H, s), 1.11 (9H, s). $^{13}$C NMR (600 Mz, MeOH-d$_4$) δ 214.98, 214.75, 166.37, 160.59, 160.53, 160.48, 160.42, 152.97, 152.84, 146.77, 146.72, 142.97, 142.78, 137.05, 136.05, 136.84, 136.79, 131.94, 131.82, 131.64, 131.60, 129.39, 129.34, 129.02, 128.95, 128.09, 126.43, 114.51, 114.48, 114.33, 103.68, 103.52, 88.80, 88.77, 88.26, 88.04, 87.50, 87.40, 77.90, 77.33, 75.15, 74.87, 72.99, 70.54, 55.80, 44.50, 44.10, 27.34, 26.81. HRMS [M+Na]$^+$ calculated for C$_{35}$H$_{38}$N$_2$O$_9$ 653.2475. Found 653.2484. FIG. 11A shows the $^1$H NMR spectrum of 93, FIG. 11B shows the $^{13}$C NMR spectrum, and FIG. 11C shows the HRMS of 93.

Synthesis of (2R,3R,4R,5S)-4-(bis(4-methoxyphenyl)(phenyl)methoxy)-5-(3,3-dimethyl-2-oxo-1-(phosphonooxy)butyl)-2-(2,4-dioxo-3,4-dihydropyrimidin-1(2H)-yl)tetrahydrofuran-3-yl acetate 94

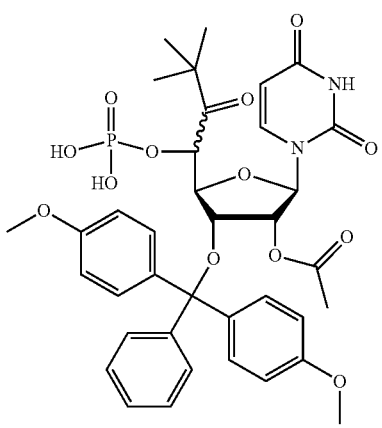

94

Figure 12A:
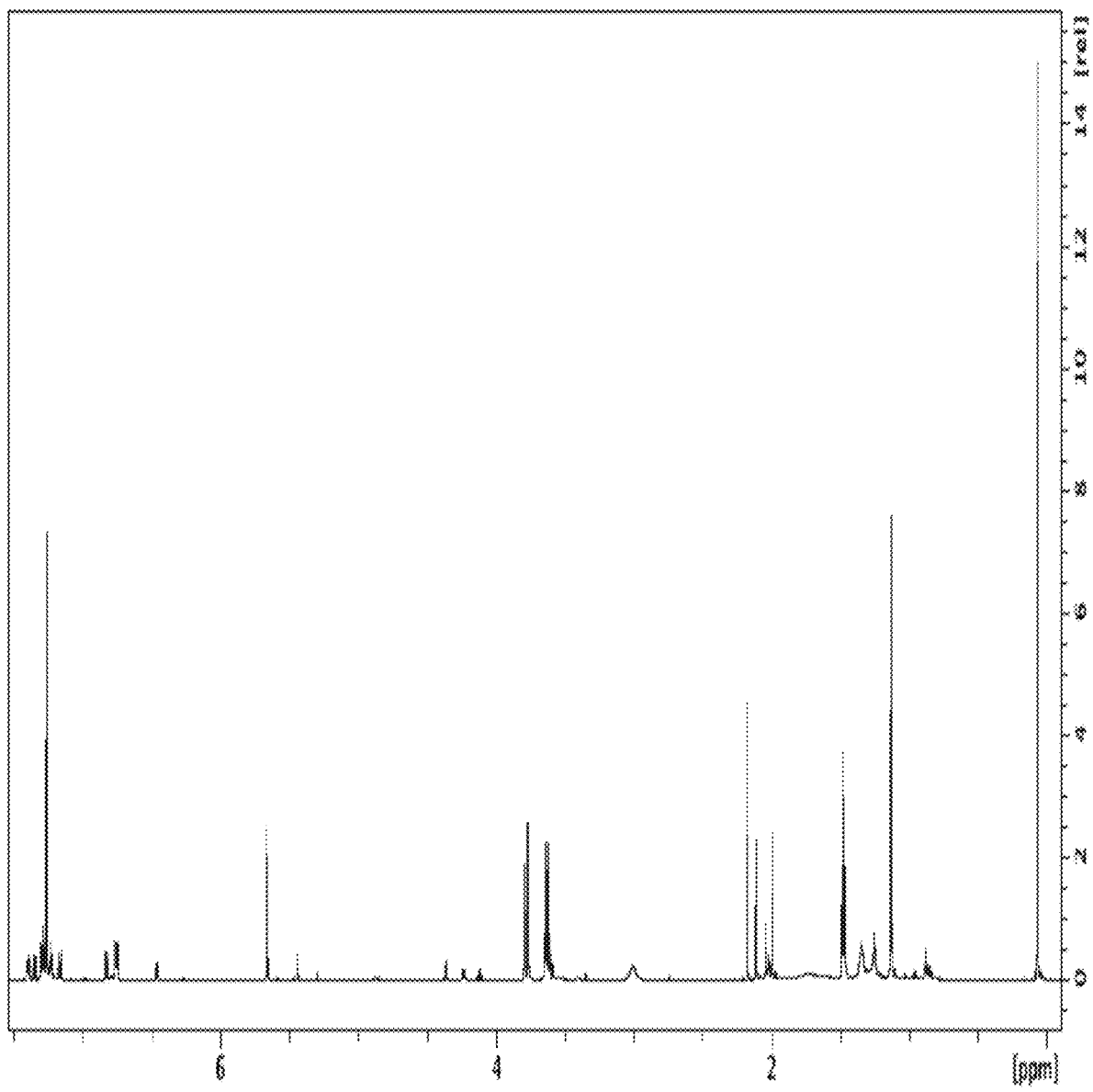
FIGS. 12A-12D: $^1$H NMR (FIG. 12A), $^{13}$C NMR (FIG. 12B), $^{31}$P NMR (FIG. 12C), and HRMS spectra (FIG. 12D) of 94.
Figure 12B:
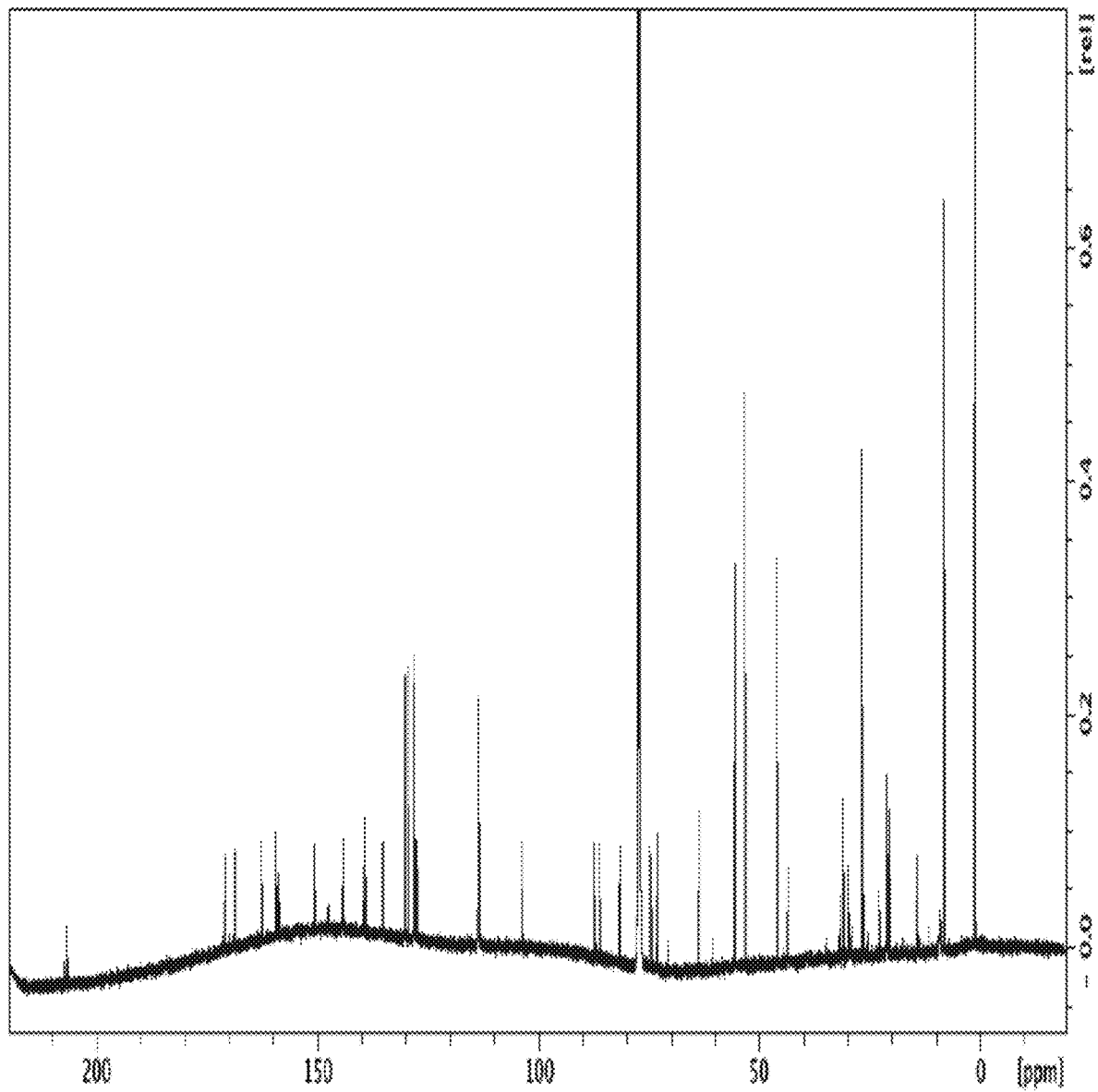
Figure 12C:
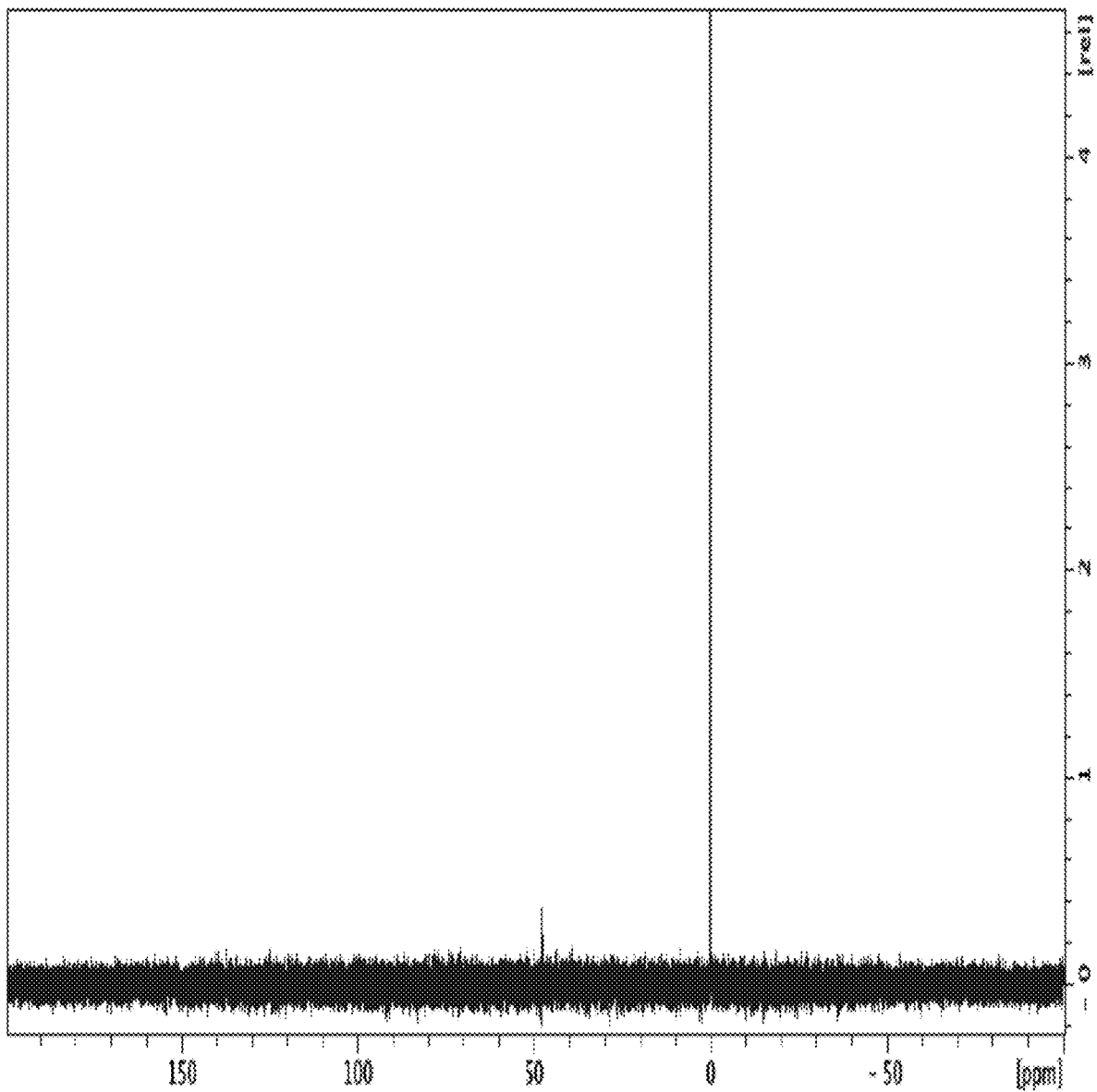
Figure 12D:
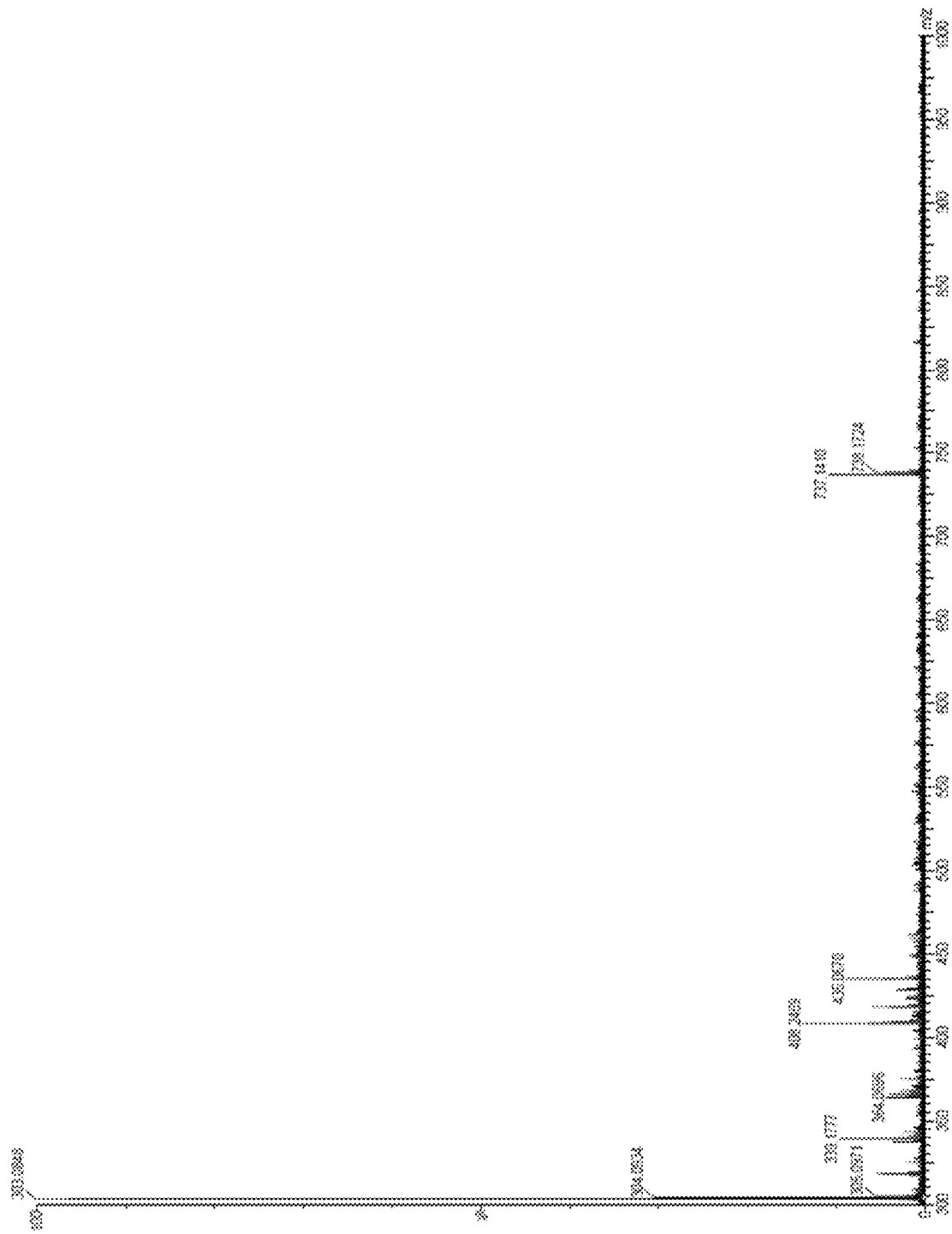

0.06 g (0.095 mmol) 93 and 2.50 mg (0.02 mmol) DMAP were dissolved in 8.0 mL of DCM. 10 µL of acetic anhydride and 20 µL of triethylamine were added and the reaction was stirred for 126 hr until quenched with methanol and concentrated. The reaction mixture was run through a silica column using an eluent of 30% to 40% ethyl acetate in hexane with 5% triethylamine then 1% to 3% methanol in 40/60 ethyl acetate/hexane with 5% triethylamine After concentrating, the crude product was used directly in the next step. 0.07 g (1.03 mmol) imidazole was coevaporated with acetonitrile twice then dissolved in 3.0 mL of DCM and submerged in an ice salt bath. 0.03 mL of phosphorous trichloride (PCl$_3$) was added slowly followed by 0.15 mL of triethylamine in 0.15 mL of DCM. This solution was allowed to stir for 30 min. Then 0.06 g (0.089 mmol) of the nucleoside was coevaporated separately in toluene twice and dissolved in 2.0 mL of DCM. This was added dropwise to the stirring solution. After 1 hour, the flask was removed from the ice bath and 6.0 mL of triethylammonium bicarbonate buffer (TEAB) was added. The organic layer was separated and washed with an equal volume of triethylammonium bicarbonate buffer again then concentrated. The H-phosphonate compound was purified on a silica column using an eluent of 0% to 8% methanol in dichloromethane with 5% triethylamine, leading to its oxidation. 27% yield. $^1$H NMR (600 Mz, CDCl$_3$) δ 7.40 (1H, d, J=1.9), 7.39 (1H, d, J=1.4), 7.35 (1H, d, J=8.3), 7.30 (2H, d, J=9.1), 7.29 (2H, d, J=8.6), 7.24 (3H, t, J=5.7), 6.77 (2H, d, J=3.5), 6.75 (2H, d, J=3.5), 6.46 (1H, d, J=8.3), 6.27 (1H, d, J=8.4), 5.66 (1H, d, J=8.3), 5.59 (1H, d, J=8.3), 5.46 (1H, d, J=3.8), 5.43 (1H, d, J=2.4), 4.38 (1H, d, J=5.6), 4.36 (1H, d, J=2.2), 4.23 (1H, dd, J=8.2, 5.2), 3.77 (3H, s), 3.76 (3H, s), 3.63 (6H, q, J=7.5), 3.59 (1H, d, J=5.5), 2.17 (3H, s), 2.10 (3H, s), 2.04 (3H, s), 1.99 (3H, s), 1.47 (9H, t, J=7.0), 1.13 (9H, s), 1.12 (9H, s). $^{13}$C NMR (600 Mz, CDCl$_3$) δ 207.21, 206.66, 170.63, 168.51, 162.37, 159.12, 158.75, 150.46, 144.11, 139.57, 139.10, 135.15, 135.06, 130.10, 130.07, 129.26, 128.13, 128.12, 127.99, 127.89, 127.63, 127.22, 113.41, 113.39, 113.29, 103.62, 87.38, 86.03, 81.51, 74.73, 74.41, 72.93, 55.44, 55.40, 53.13, 45.97, 43.53, 26.83, 26.48, 21.11, 20.65, 8.28. $^{31}$P NMR (400 Mz, CDCl$_3$) δ 47.9, 9.3. HRMS [M+H]$^+$ calculated for C$_{37}$H$_{41}$N$_2$O$_{12}$P 737.2475. Found 737.1410. FIG. 12A shows the $^1$H NMR spectrum of 94, FIG. 12B shows the $^{13}$C NMR spectrum, FIG. 12C shows the $^{31}$P NMR spectrum, and FIG. 12D shows the HRMS of 94.

Synthesis of a2R,3R,4R,5R)-3-(bis(4-methoxyphenyl)(phenyl)methoxy)-4-((tertbutyldimethylsilyl)oxy)-5-(2,4-dioxo-3,4-dihydropyrimidin-1(2H)-yl)tetrahydrofuran-2-yl)methyl phosphonate triethylammonium salt 95

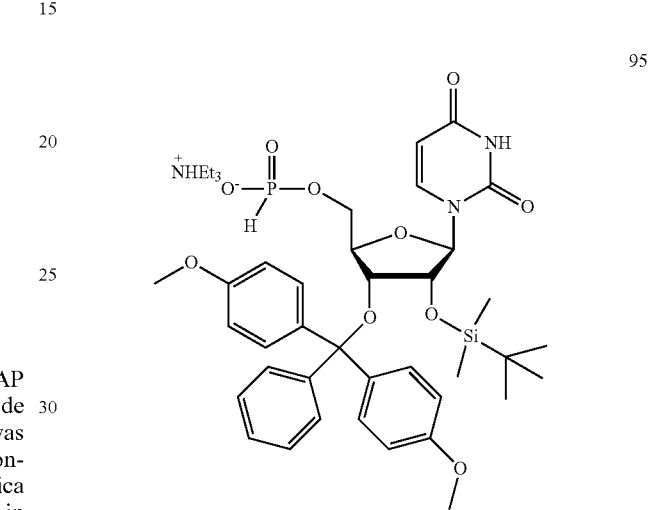

95

Figure 13A:
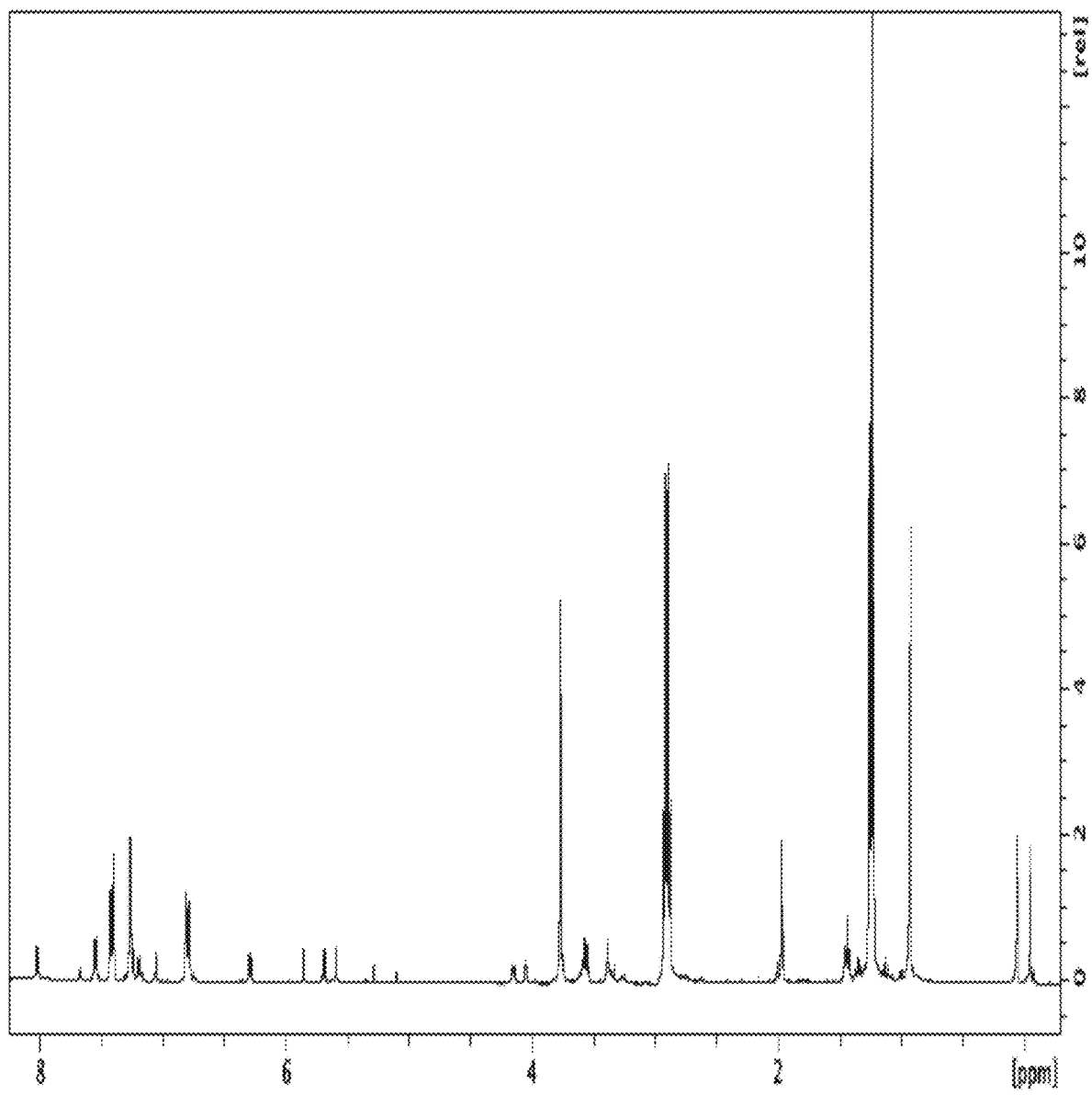
FIGS. 13A-13D: $^1$H NMR (FIG. 13A), $^{13}$C NMR (FIG. 13B), $^{31}$P NMR (FIG. 13C), and HRMS spectra (FIG. 13D) of 95.
Figure 13B:
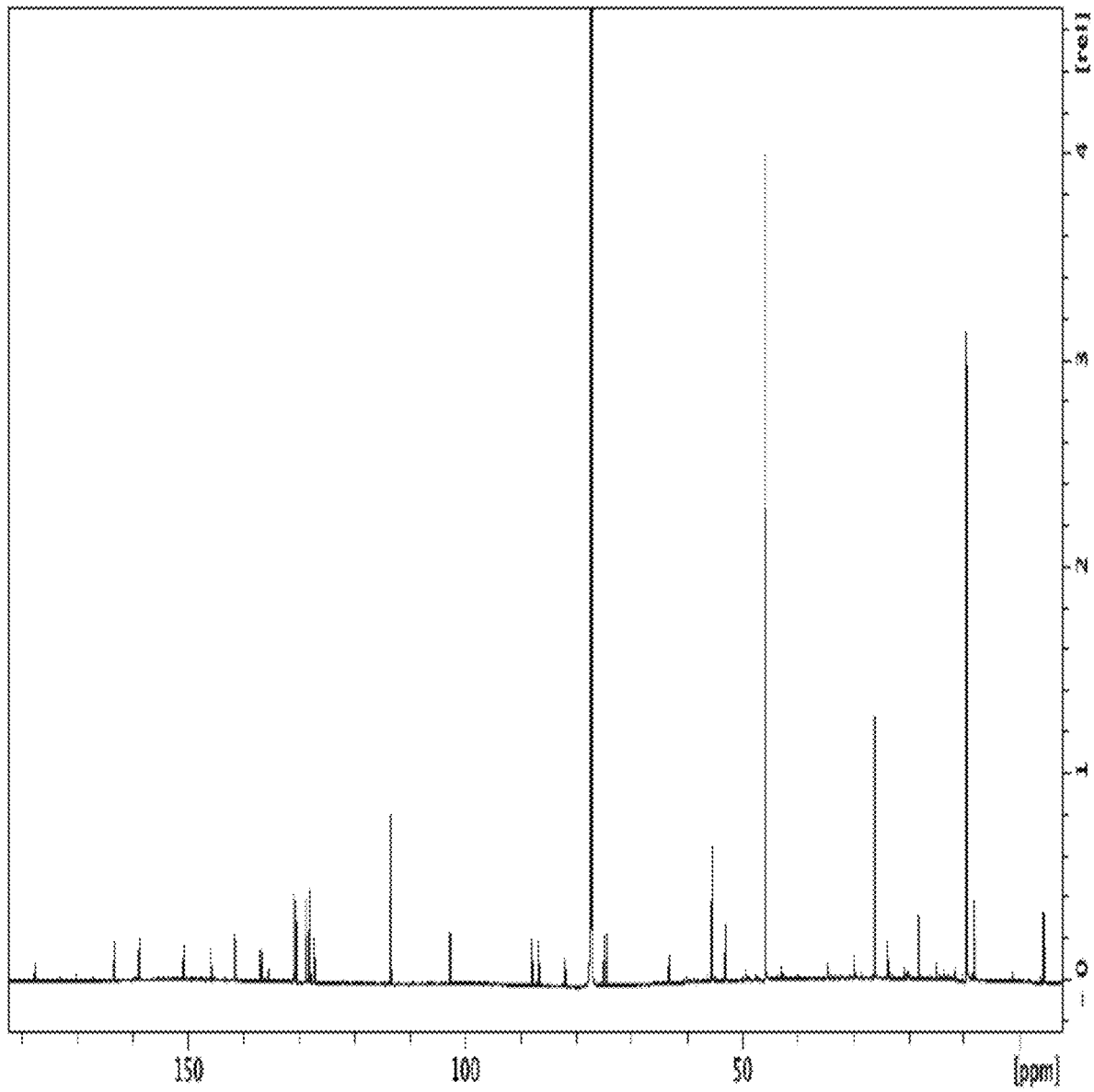
Figure 13C:
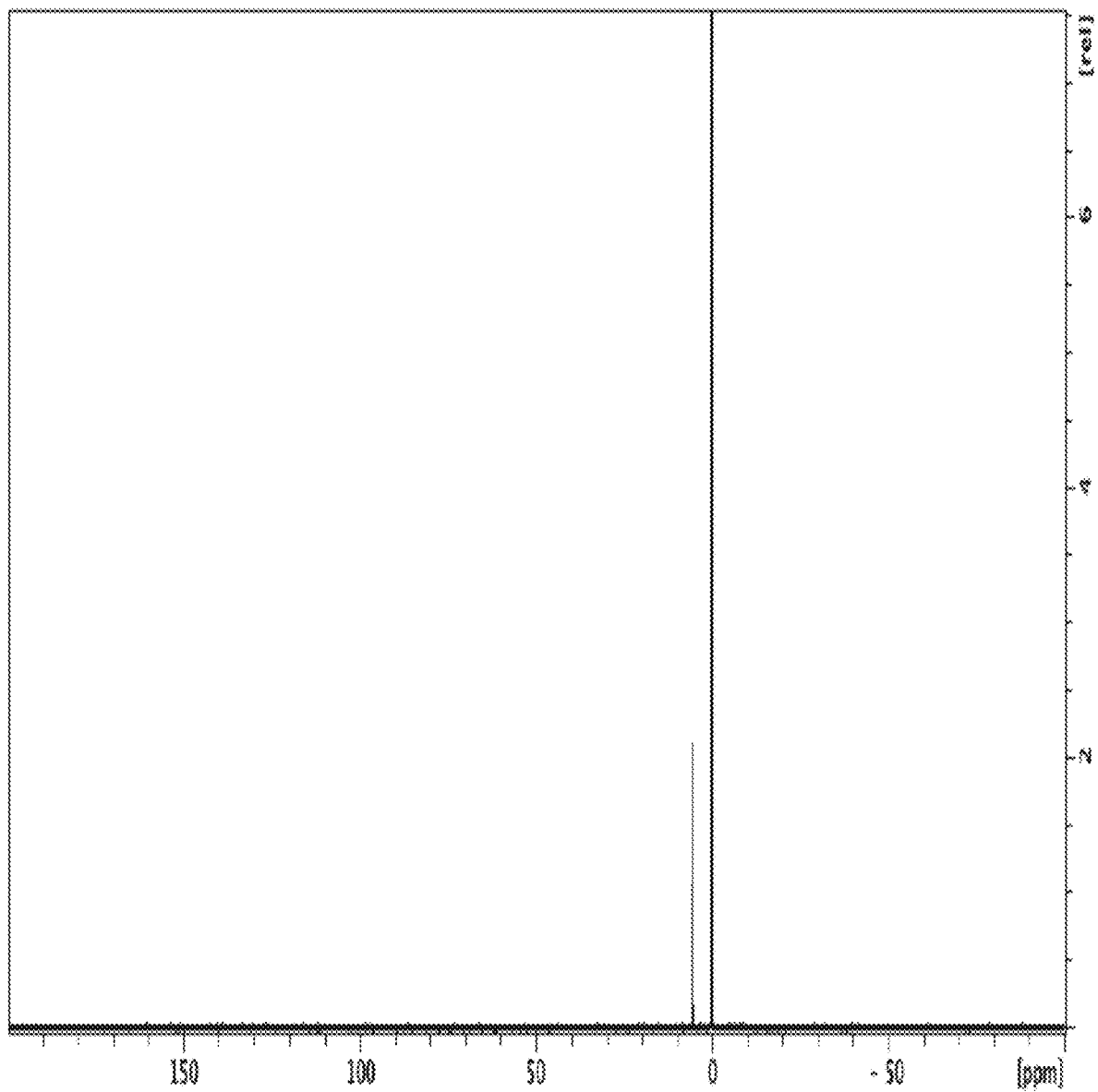
Figure 13D:
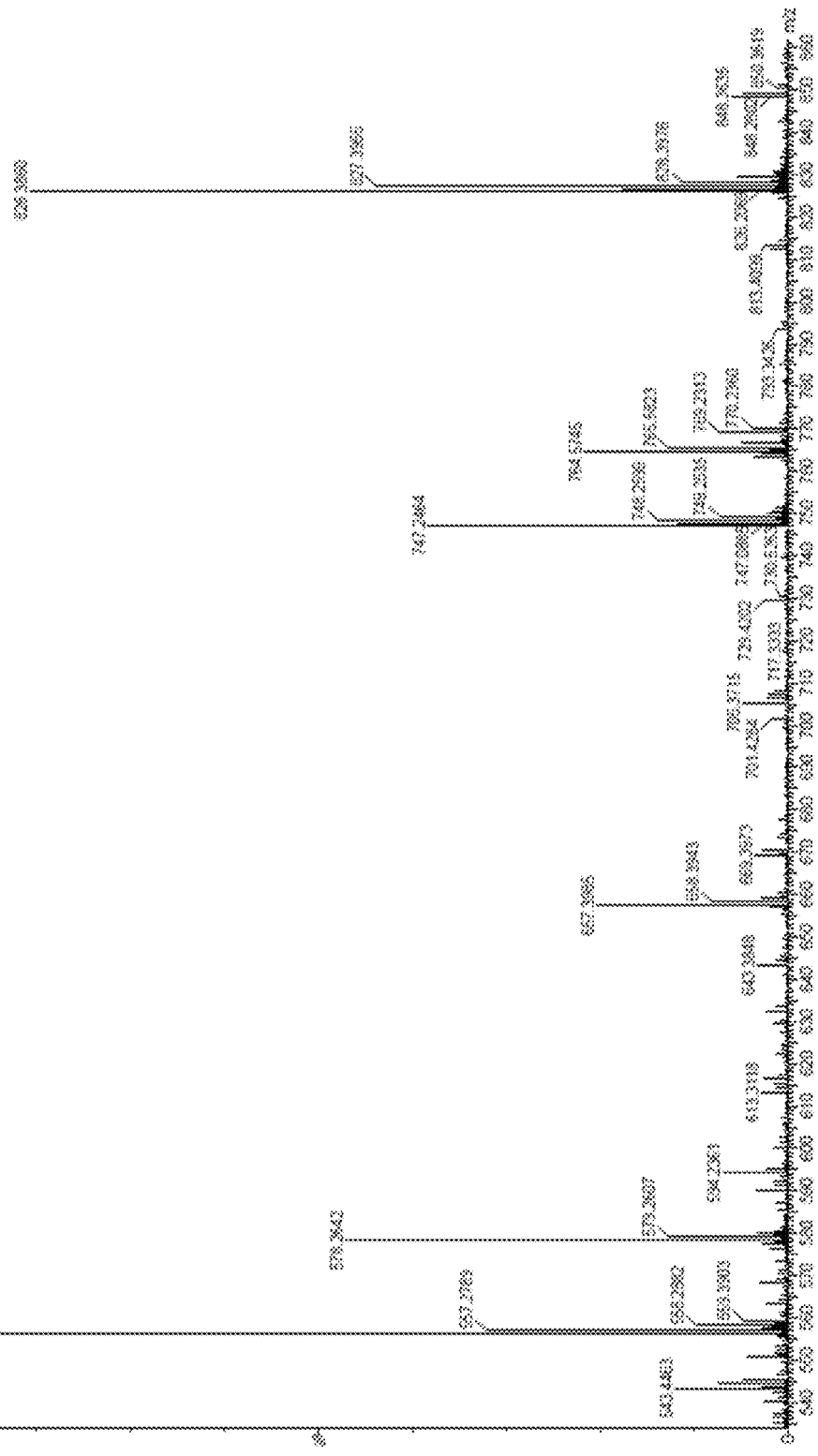

0.28 g (5.88 mmol) imidazole was coevaporated in toluene three times then dissolved in 10.0 mL of DCM and submerged in an ice salt bath. 0.15 mL of phosphorous trichloride was added dropwise followed by 0.85 mL of triethylamine. The reaction was left to stir for 30 min then 0.21 g (0.50 mmol) 2'-O-TBDMS-3'-O-DMTr-Uridine was coevaporated separately three times in toluene and dissolved in 7.0 mL of DCM before adding to the solution dropwise. Reaction was left stirring for 85 min and then brought to room temperature and quenched with 25 mL of TEAB. The DCM layer was separated and washed with an equal volume of TEAB again then concentrated. Compound was purified on a silica column using an eluent of 0-8% methanol in dichloromethane with 3% triethylamine 99% yield. $^1$H NMR (400 Mz, CDCl$_3$) δ 8.01 (1H, d, J=8.1), 7.54 (2H, d, J=7.5), 7.41 (4H, d, J=8.8), 7.25 (3H, t, J=8.1), 6.79 (4H, d, J=8.1), 6.29 (1H, d, J=8.1), 5.69 (1H, d, J=8.1), 4.15 (1H, dd, J=6.4, 5.0), 4.04 (1H, d, J=5.0), 3.76 (6H, s), 3.74 (1H, d, J=4.9), 3.56 (1H, d, J=7.1), 3.38 (1H, unresolved d), 2.90 (6H, q, J=14.1, 7.1), 1.23 (9H, t, J=7.3), 0.92 (9H, s), 0.05 (3H, s), −0.06 (3H, s). $^{13}$C NMR (600 Mz, CDCl$_3$) δ 163.29, 158.83, 150.75, 145.67, 141.50, 136.98, 136.56, 113.40, 102.62, 87.85, 86.72, 81.97, 74.90, 74.31, 63.15, 55.43, 45.76, 29.89, 26.05, 9.48, −4.17, −4.38. $^{31}$P NMR (400 Mz, CDCl$_3$) δ 5.6. HRMS [M+H]$^+$ calculated for C$_{42}$H$_{60}$N$_3$O$_{10}$PSi 826.3858. Found 826.3860. FIG. 13A shows the $^1$H NMR spectrum of 95, FIG. 13B shows the $^{13}$C NMR spectrum, FIG. 13C shows the $^{31}$P NMR spectrum, and FIG. 13D shows the HRMS of 95.

Certain embodiments of the compositions and methods disclosed herein are defined in the above examples. It should be understood that these examples, while indicating particular embodiments of the invention, are given by way of illustration only. From the above discussion and these examples, one skilled in the art can ascertain the essential characteristics of this disclosure, and without departing from the spirit and scope thereof, can make various changes and modifications to adapt the compositions and methods described herein to various usages and conditions. Various changes may be made and equivalents may be substituted for elements thereof without departing from the essential scope of the disclosure. In addition, many modifications may be made to adapt a particular situation or material to the teachings of the disclosure without departing from the essential scope thereof.

What is claimed is:

1. A composition comprising Formula I:

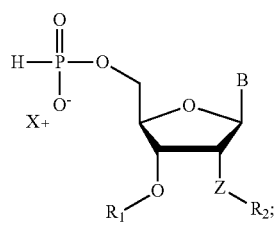

Formula I wherein:
X is a trialkylammonium having a formula of $NHR_3$, wherein $R_3$ is alkyl;
Z is nitrogen with hydrogens to satisfy the valence of the nitrogen, or fluorine;
$R_1$ is a protecting group; and
B is hydrogen, a nucleobase, aryl, or a heterocycle optionally protected;

or a stereoisomer, racemate, hydrate, solvate, polymorph, or prodrug thereof.

2. The composition of claim 1, wherein $R_1$ is dimethoxytrityl, monomethoxytrityl, or trimethoxytrityl.

3. A method for synthesizing an oligonucleotide, the method comprising:
linking a protected first nucleoside through a first linker to a support to form a support-bound, protected first nucleoside;
deprotecting the support-bound, protected first nucleoside by treating the support-bound, protected first nucleoside with a halogenated carboxylic acid in dichloromethane to free a 3' hydroxyl of the support-bound, protected first nucleoside;
phosphonating a protected second nucleoside by reacting the protected second nucleoside with phosphorus trichloride to form a protected second nucleoside having a 5'-H-phosphonate, wherein the protected second nucleoside has Formula I:

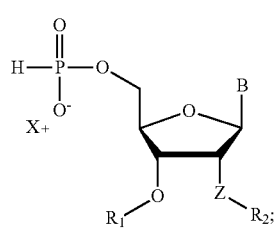

Formula I wherein:
X is a trialkylammonium having a formula of $NHR_3$, wherein $R_3$ is alkyl;
Z is oxygen;
$R_1$ is a protecting group;
$R_2$ is tert butyl dimethyl silyl (TBDMS), triisopropylsilyl oxymethylene, fluorenylmethyloxycarbonyl (Fmoc), alkyl, aryl, or acetyl; and
B is hydrogen, a nucleobase, aryl, or a heterocycle optionally protected;
coupling the protected second nucleoside to the first nucleoside to form a first H-phosphonate linkage;
capping unreacted 3' ends by esterification to incorporate capping groups thereon;
oxidizing the first H-phosphonate linkage to produce an oligonucleotide; and
optionally, repeating the deprotection, coupling, capping, and oxidizing steps to produce an oligonucleotide having a desired sequence.

4. The method of claim 3, wherein the protected second nucleoside is activated prior to coupling with adamantyl chloride.

5. The method of claim 3, wherein the protected second nucleoside is a 3'-dimethoxytrityl-5'-H-phosphonate salt prior to the coupling.

6. The method of claim 3, wherein the repeating comprises coupling a third nucleoside to the protected second nucleoside to form a second H-phosphonate linkage, wherein the third nucleoside comprises a 5'-H-phosphonate prior to the coupling.

7. The method of claim 3, further comprising removing the support.

8. The method of claim 3, further comprising subjecting the oligonucleotide to a silyl deprotection step.

9. The method of claim 3, wherein the support-bound, protected first nucleoside comprises a 3'-DMTr protected nucleoside.

10. The method of claim 3, wherein the protected second nucleoside is activated using a bulky carboxylic acid chloride.

11. The method of claim 3, wherein the oxidizing is conducted prior to addition of a third nucleoside.

12. The method of claim 3, wherein the oxidizing is conducted following addition of a third or subsequent nucleoside.

13. The method of claim 3, further comprising removing the capping groups.

14. A method for making a 5'-H-phosphonate, the method comprising:
protecting a nucleoside at a 2' position with a first protecting group to form a 2'-protected nucleoside;
protecting the 2'-protected nucleoside at a 5' position to form a fully protected nucleoside;
hydrolyzing the fully protected nucleoside in acid with heat to form a hydrolyzed protected nucleoside;
silylating the hydrolyzed protected nucleoside at the 2' position to form a silylated nucleoside;
protecting the silylated nucleoside with a second protecting group to form a protected silylated nucleoside;
deprotecting the protected silylated nucleoside to form a 5' hydroxyl nucleoside; and
phosphonating the 5' hydroxyl nucleoside by reacting the 5' hydroxyl nucleoside with phosphorus trichloride to form a 5'-H-phosphonate.

15. The method of claim 14, wherein the nucleoside comprises uridine, cytidine, adenosine, or guanosine.

16. The method of claim 14, wherein the 5'-H-phosphonate comprises Formula I:

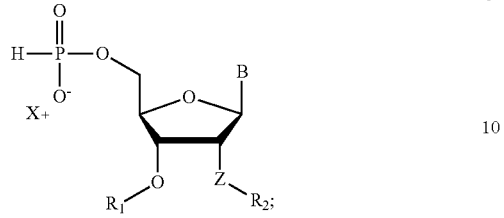

Formula I wherein:
- X is a trialkylammonium having a formula of $NHR_3$, wherein $R_3$ is alkyl;
- Z is oxygen;
- $R_1$ is a protecting group;
- $R_2$ is tert butyl dimethyl silyl (TBDMS), triisopropylsilyl oxymethylene, fluorenylmethyloxycarbonyl (Fmoc), alkyl, aryl, or acetyl; and
- B is hydrogen, a nucleobase, aryl, or a heterocycle optionally protected.

* * * * *